(12) United States Patent
Dey et al.

(10) Patent No.: US 8,617,898 B2
(45) Date of Patent: Dec. 31, 2013

(54) QUANTITATIVE ANALYSIS OF VITAMIN D3, VITAMIN D2, AND METABOLITES THEREOF

(75) Inventors: Subhakar Dey, N. Billerica, MA (US); Sasi K. Pillai, Littleton, MA (US); Brian Williamson, Ashland, MA (US); Subhasish Purkayastha, Acton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 368 days.

(21) Appl. No.: 13/013,664

(22) Filed: Jan. 25, 2011

(65) Prior Publication Data

US 2011/0183429 A1 Jul. 28, 2011

Related U.S. Application Data

(60) Provisional application No. 61/297,917, filed on Jan. 25, 2010.

(51) Int. Cl.
*G01N 33/00* (2006.01)
*G01N 30/72* (2006.01)

(52) U.S. Cl.
USPC ............ 436/131; 436/71; 436/127; 436/128; 436/161; 436/173; 436/174; 436/177; 436/178; 436/181

(58) Field of Classification Search
USPC ........... 436/71, 127–128, 131, 161, 173–174, 436/177–178, 181
See application file for complete search history.

(56) References Cited

U.S. PATENT DOCUMENTS

| | | | | |
|---|---|---|---|---|
| 4,366,320 A * | 12/1982 | Gilbertson | ................ | 548/263.6 |
| 4,554,106 A | 11/1985 | Deluca | | |
| 4,772,433 A * | 9/1988 | Hesse | ............ | 544/233 |
| 5,187,086 A * | 2/1993 | Janda | ............ | 435/146 |
| 5,635,404 A * | 6/1997 | Wilson | ............ | 436/173 |
| 5,880,270 A | 3/1999 | Berninger | | |
| 7,019,146 B1 * | 3/2006 | Ishigai et al. | ................ | 548/103 |
| 7,309,608 B2 | 12/2007 | Nguyen | | |
| 7,556,969 B2 * | 7/2009 | Wang et al. | ............ | 436/173 |
| 7,972,868 B2 * | 7/2011 | Holmquist et al. | ............ | 436/173 |
| 2001/0007907 A1 * | 7/2001 | Reddy et al. | ............ | 552/653 |
| 2004/0157344 A1 * | 8/2004 | Wang et al. | ............ | 436/518 |
| 2005/0048489 A1 * | 3/2005 | Thompson et al. | ............ | 435/6 |
| 2005/0261250 A1 | 11/2005 | Daifotis | | |
| 2006/0263886 A1 * | 11/2006 | Peters et al. | ............ | 436/56 |
| 2008/0014642 A1 | 1/2008 | Purkayastha | | |
| 2009/0111129 A1 * | 4/2009 | Green et al. | ............ | 435/7.31 |

(Continued)

OTHER PUBLICATIONS

Aberhart, D. J. et al, Journal of Organic Chemistry 1976, 41, 2098-2102.*

(Continued)

*Primary Examiner* — Arlen Soderquist

(57) ABSTRACT

Quantification of vitamin D2, vitamin D3, and the monohydroxy and diihydroxy metabolites of vitamin D2 and vitamin D3, can comprise labeling analytes with mass spectrometry (MS) tagging reagents and performing LC-MSMS analysis of the labeled analytes. The labeled analytes can include a labeled standard and can have distinct retention times on a reversed phase column, as well as distinct masses. Under high energy collisions, reporter groups can be generated. The intensity or the peak area detected for each reporter group can be used for quantitation. In some embodiments, a one-step tagging reagent is used that is a dienophile-containing, labeled Diels Alder reagent.

43 Claims, 31 Drawing Sheets

(56) References Cited

U.S. PATENT DOCUMENTS

| | | |
|---|---|---|
| 2009/0137056 A1 | 5/2009 | Holmquist |
| 2011/0133068 A1* | 6/2011 | Holmquist et al. ............ 250/282 |
| 2011/0240840 A1* | 10/2011 | Holmquist et al. ............ 250/282 |
| 2011/0301063 A1* | 12/2011 | Netzel et al. .................... 506/12 |

OTHER PUBLICATIONS

Kuhrau, M. et al, Polymer International 1991, 26, 75-79.*
Aebersold, R. et al, Protien Science 1992, 1, 494-503.*
Mallakpour, S. E. et al, Journal of Science Islamic Republic of Iran 1993, 4, 199-205.*
Vreeken, R. J. et al, Biological Mass Spectrometry 1993, 22, 621-632.*
Mamer, O. A. et al, Journal of the American Society for Mass Spectrometry 1994, 5, 292-298.*
Zaia, J. et al, Journal of the American Society for Mass Spectrometry 1995, 6, 428-436.*
Wang, K. et al, Analytical Biochemistry 1996, 243, 28-40.*
Roth, K. W. D. et al, Mass Spectrometry Reviews 1998, 17, 255-274.*
Higashi, T. et al, Biomedical Chromatography 2001, 15, 133-140.*
Higashi, T. et al, Journal of Chromatography B 2002, 772, 229-238.*
Suzuki, Y. et al, Kagaku Kogyo 2003, 54,433-438.*
Murao, N. et al, Analytical Biochemistry 2005, 346, 158-166.*

* cited by examiner

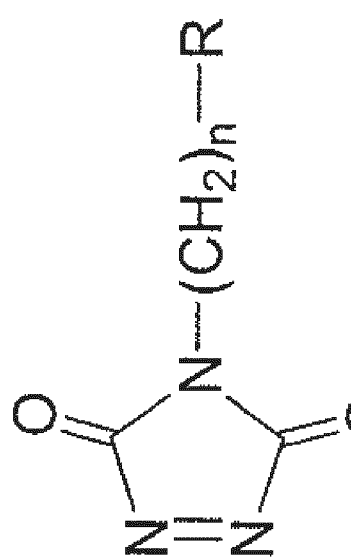
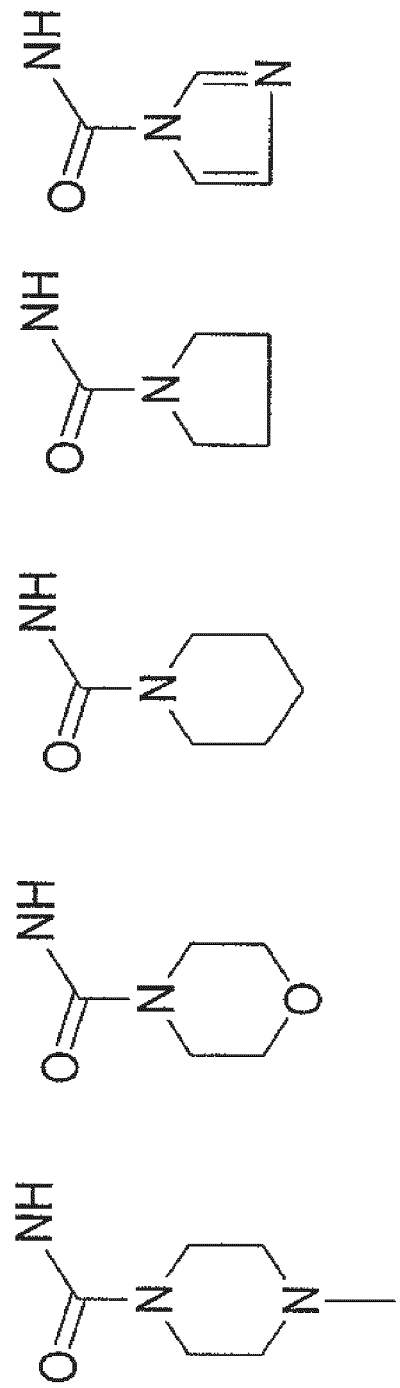
FIG. 12B

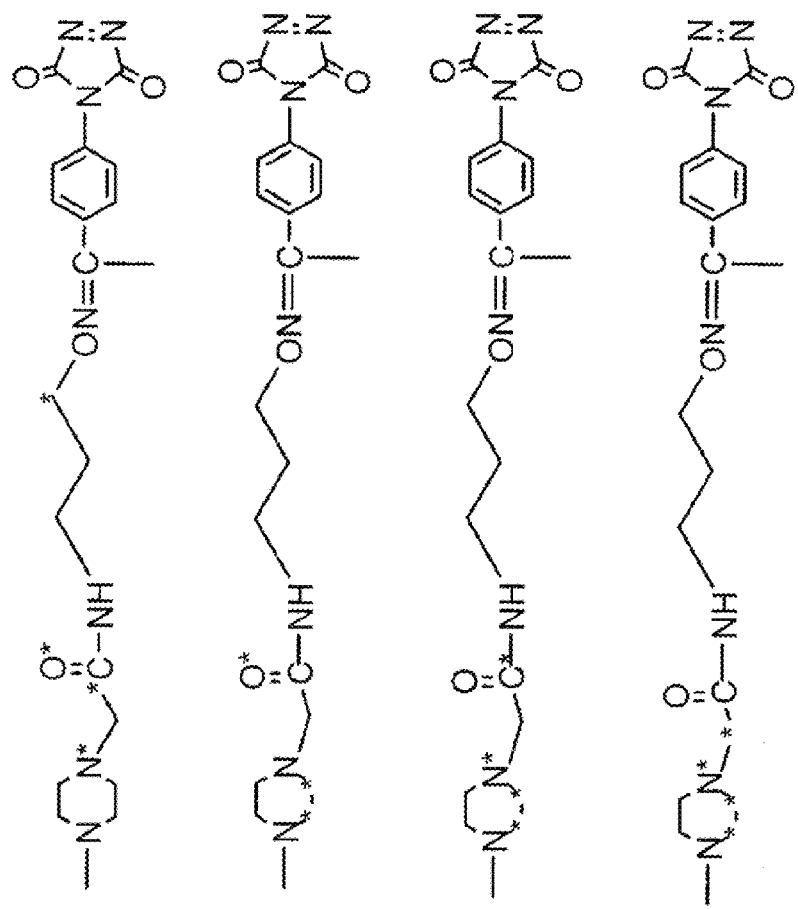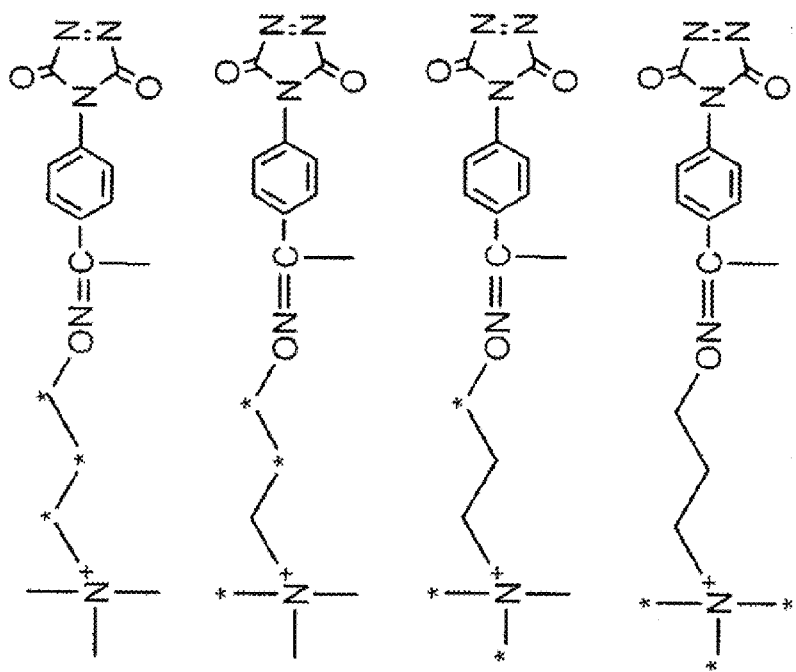
FIG. 17

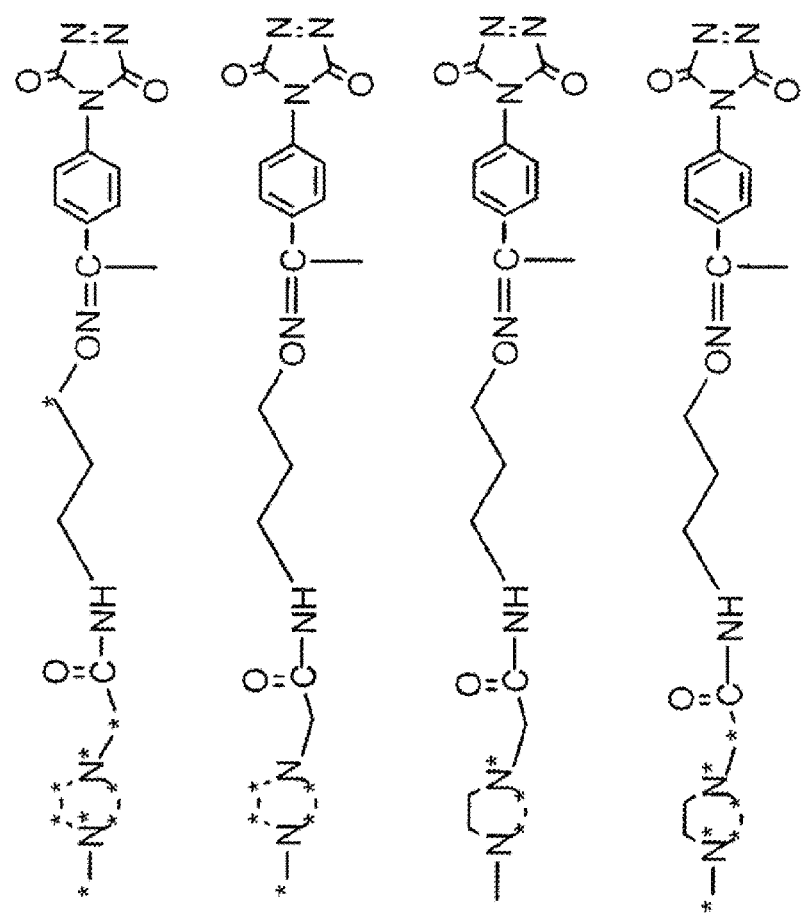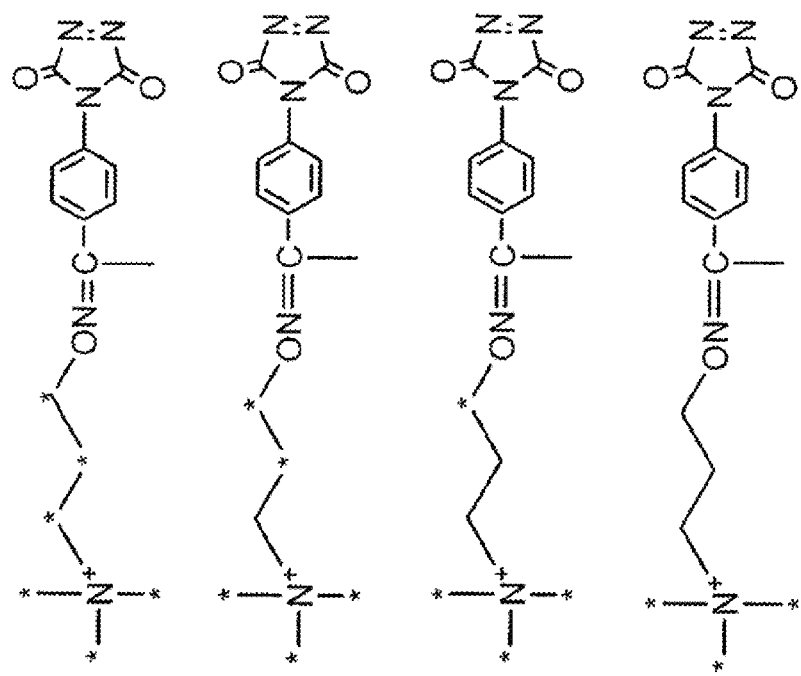
FIG. 18

| Sample and Transition (strongest transition) | Concentration (on column) | Areas of three injections | | | Average area of three injections |
|---|---|---|---|---|---|
| 1α, 25 DiHyVD₃ 399.6→135.2 | 10 pg | | | | Low to detect |
| | 25 pg | 6.89 e2 | 5.80 e2 | 5.88 e2 | 6.19 e2 |
| | 50 pg | 1.20 e3 | 1.15 e3 | 1.13 e3 | 1.16 e3 |
| 1α, 25 DiHyVD₃_PTAD 592.5→574.4 | 10 pg | 4.13 e3 | 6.04 e3 | 5.44 e3 | 5.20 e3 |
| | 25 pg | 1.02 e4 | 1.21 e4 | 1.01 e4 | 1.08 e4 |
| | 50 pg | 2.21 e4 | 2.18 e4 | 2.14 e4 | 2.18 e4 |
| 1α, 25 DiHyVD₃_QAO-C 748.6→689.5 | 10 pg | 4.36 e4 | 5.70 e4 | 5.49 e4 | 5.19 e4 |
| | 25 pg | 8.97 e4 | 1.06 e5 | 1.05 e5 | 1.00 e5 |
| | 50 pg | 2.52 e5 | 2.63 e5 | 2.60 e5 | 2.58 e5 |

Average X 18
Average X 192
Average X 11

- Instrument: API 4000
- Reactions done in Acetonitrile
- Same stock solution of 1α, 25 DiHyVD₃ and pipettes used for all reactions
- Similar concentrations of PTAD (Cookson) and QAO-Cookson used
- All reactions and MS analysis done in same batch/day to keep the variability low

PTAD          QAO-Cookson

FIG. 20

QUANTITATIVE ANALYSIS OF VITAMIN D3, VITAMIN D2, AND METABOLITES THEREOF

CROSS-REFERENCE TO RELATED APPLICATION

The present application claims benefit from earlier filed U.S. Provisional Patent Application No. 61/297,917, filed Jan. 25, 2010, which is incorporated herein in its entirety by reference.

FIELD

The present teachings relate to the fields of mass spectrometry and tagging reagents useful for mass spectrometry.

BACKGROUND

Analysis of the vitamin D family of metabolites, including, vitamin D3, vitamin D2, and metabolites of vitamin D3 and vitamin D2, such as the 25-hydroxy and the 1,25 dihydroxy analogs, has conventionally been difficult because these analytes are present at low levels in a determining matrix such as plasma. Conventional methods of analyzing vitamin D3, vitamin D2, and their metabolites suffer additional drawbacks. Immunoassays and LC/UV methods used to analyze vitamin D3 and its metabolites, for example, are not specific and suffer from sample treatment complexity. Also strategies involving LC/MSMS for exploiting derivatization of the analytes have failed to achieve the limit of detection required for the assay to be viable in a clinical setup and also lack multiplexing capability (Shimada, et.al., *Analyst*, December 1991, Vol 116, 1393-1397; Higashi et al., *Chem. Pharm. Bull.*, 54(11), 1479-1485 (2006)). A need exists for a method of quantitating these analytes that overcomes these drawbacks.

It has been found that two functionalities in vitamin D3, vitamin D2, and metabolites of vitamin D3 and vitamin D2, which can be exploited for derivatization, include the hydroxyl group and the conjugated diene functionality. The Cookson reagent described by Shimada, et al. and Higashi et al. takes advantage of Diels-Alder chemistry to add a triazolone derivative across the diene functionality in vitamin D3, vitamin D2, and their metabolites.

SUMMARY

According to various embodiments, the methods of the present teachings provide a method to quantify vitamin D2, vitamin D3, and metabolites thereof, herein collectively referred to as vitamin D analytes. The metabolites can comprise, for example, the monohydroxy and dihydroxy metabolites of vitamin D2 and vitamin D3. Quantification of vitamin D2, vitamin D3, and the monohydroxy and dihydroxy metabolites of vitamin D2 and vitamin D3 can comprise labeling the analytes using mass spectrometry (MS) tagging reagents, and LC-MSMS analysis of the labeled analytes using a Multiple Reaction Monitoring (MRM) workflow. The labeled analytes can have distinct retention times on a reversed phase column, and distinct masses. Under high energy collision, reporter groups can be generated. The intensity or the peak area detected for each reporter group can be used not only for identification, but also for quantitation.

In some embodiments, a two-step derivatization process is provided that takes advantage of the diene functionality in the family of vitamin D analytes. In some embodiments, vitamin D analytes are derivatized in a one-step process. Quantitation of the analytes in a test sample can be achieved using an LC-MSMS and MRM workflow. The reagent design increases sensitivity of an assay and provides multi-plexing capability.

BRIEF DESCRIPTION OF THE DRAWINGS

The present teachings will be more fully understood with reference to the appended drawings. The drawings are intended to illustrate, not limit, the present teachings.

FIG. 12B shows a general formula and exemplary substituents that can be used in a one-step tagging method for vitamin D analytes.

FIG. 17 shows two different sets of exemplary isobaric tags, each set comprising four different reagents that can be used in a four-plex assay, according to various embodiments of the present teachings.

FIG. 18 shows two different sets of exemplary mass differential tags, each set comprising four different reagents that can be used in a four-plex assay, according to various embodiments of the present teachings.

FIG. 20 shows a comparison of the sensitivity of QAO-C derivatized 1α,25-DihydroxyVitamin-$D_3$, PTAD 1α,25-DihydroxyVitamin-$D_3$, and underivatized 1α,25-DihydroxyVitamin-$D_3$, according to various embodiments of the present teachings.

DETAILED DESCRIPTION

Figure 1:
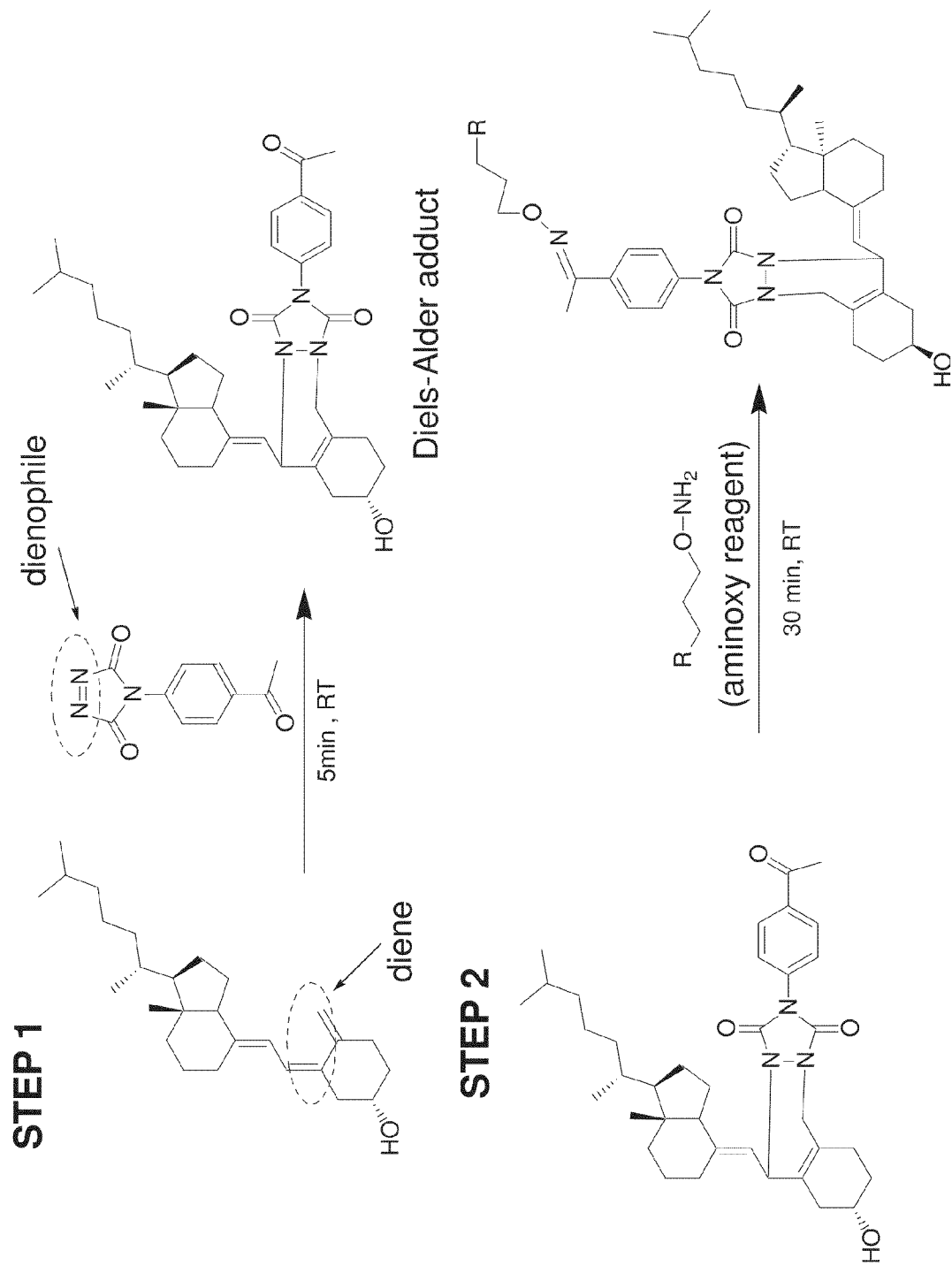
FIG. 1 shows a reaction scheme for a two-step chemical reaction that can be used to label vitamin D analytes according to various embodiments of the present teachings.

According to various embodiments, a method for quantitating a vitamin D analyte in a sample is provided. The vitamin D analyte can comprise one or more of vitamin D2, vitamin D3, a metabolite of vitamin D2, and a metabolite of vitamin D3. In some embodiments, the method comprises treating a vitamin D analyte with a dienophile reagent to form a Diels-Alder adduct. The Diels-Alder adduct is then labeled with an aminoxy mass spectrometry (MS) tagging reagent to form a labeled adduct. The labeled adduct is then analyzed using mass spectrometry. In other embodiments, a one-step tagging reagent is used, for example, a dienophile-containing, labeled Diels-Alder reagent.

According to various embodiments using a two-step chemistry, the aminoxy MS tagging reagent can comprise a compound having the following structure:

$$R-(CH_2)_n-ONH_2$$

wherein R is $R_1$, $R_2$, and $R_3$ can each independently be a hydrogen atom or an alkyl group, and n can be from 1 to 20, from 1 to 15, from 1 to 10, or from 1 to 5.

In some embodiments, the aminoxy MS tagging reagent can comprise a compound having the following structure:

$$R-(CH_2)_n-ONH_2$$

wherein R can be, but is not limited to, one or more of these five structures and n can be from 1 to 20, from 1 to 15, from 1 to 10, or from 1 to 5.

The method can further comprise providing a standard comprising a known concentration of a known vitamin D analyte, treating the known vitamin D analyte of the standard with a dienophile reagent to form a standard Diels-Alder adduct, and labeling the standard Diels-Alder adduct with an aminoxy MS tagging reagent to form a labeled standard adduct. The labeled standard can then be mixed with the adduct obtained from the sample and the labeled adduct to form a mixture. The mixture can then be separated to form separated labeled analytes, and the separated analytes can be analyzed.

In some embodiments, the aminoxy MS tagging reagent used to label the standard Diels-Alder adduct can comprise a first isobaric tag from a set of isobaric tags. The aminoxy MS tagging reagent used to label the Diels-Alder adduct from the sample can comprise a second isobaric tag from the same set of isobaric tags, but that differs from the first isobaric tag. The labeled adduct can be analyzed using mass spectrometry, using LC-MSMS analysis of the labeled adduct, using a combination thereof, or the like.

In some embodiments, parent daughter ion transition monitoring (PDITM) of the labeled analytes is performed using a triple quadrupole MS platform. More details about PDITM and its use are described in U.S. Patent Application Publication No. US 2006/0183238 A1, which is incorporated herein in its entirety by reference. In some embodiments, the aminoxy MS tagging reagent undergoes neutral loss during MSMS and leaves a reporter ion that is a charged analyte species. In some embodiments, the aminoxy MS tagging reagent forms a reporter ion that is a tag fragment during MSMS.

According to various embodiments, the vitamin D analyte can comprise a plurality of different vitamin D analytes, and the labeling can comprise labeling each with a plurality of different respective tagging reagents, for example, a different tagging reagent for each different type of analyte. The metabolites to be analyzed and for which a kit can be configured to detect, can comprise analytes of vitamin D2, for example, a monohydroxy metabolite of vitamin D2 and/or a dihydroxy metabolite of vitamin D2. In some embodiments, the metabolites are metabolites of vitamin D3 and can comprise a monohydroxy metabolite of vitamin D3 and/or a dihydroxy metabolite of vitamin D3.

According to yet other embodiments of the present teachings, a kit is provided that comprises a dienophile reagent and one or more aminoxy MS tagging reagents. The aminoxy MS tagging reagent can comprise a compound having the following structure

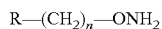

wherein R is

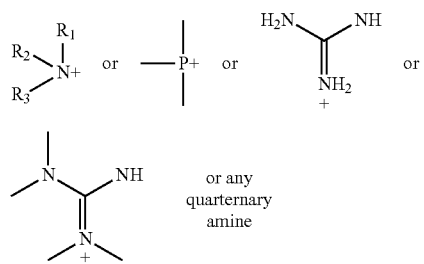

$R_1$, $R_2$, and $R_3$ can each independently be a hydrogen atom or an alkyl group, and n can be from 1 to 20, from 1 to 15, from 1 to 10, or from 1 to 5.

The kit can include an aminoxy MS tagging reagent comprising a compound having the following structure

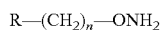

wherein R can be, but is not limited to, one or more of these five structures

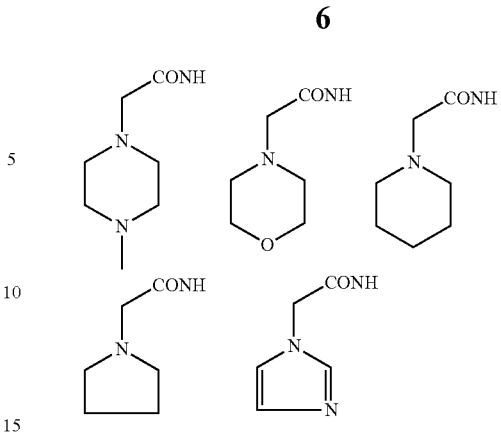

and n can be from 1 to 20, from 1 to 15, from 1 to 10, or from 1 to 5.

The kit can comprise a standard comprising a known vitamin D analyte. The standard can comprise a known concentration of a known vitamin D analyte. In some embodiments, the aminoxy MS tagging reagent included in the kit can comprise one or more isobaric tags from a set of isobaric tags. In some embodiments, the kit can comprise a plurality of different isobaric tags from a set of isobaric tags.

The kit can also comprise instructions for labeling the vitamin D analyte, for example, paper instructions or instructions formatted in an electronic file, for example, on a compact disk. In some embodiments, the kit can comprise a homogeneous assay in a single container, to which only a sample need be added. Other components of the kit can include buffers, other reagents, one or more standards, a mixing container, and the like.

According to various embodiments, the present teachings provide a method for the quantitation of one or more of vitamin D2, vitamin D3, and/or metabolites from the vitamin D family, herein collectively referred to as vitamin D analytes. Vitamin D analytes can include, for example, vitamin D2, vitamin D3, and/or the monohydroxy, dihydroxy and trihydroxy metabolites of vitamin D2 or vitamin D3 or structurally related compounds or any analyte which has a diene functionality. According to various embodiments, the method for quantification of one or more vitamin D analytes can comprise a two-step chemical reaction to modify the analytes, followed by mass analysis using mass spectrometry. According to various embodiments, the two-step chemical reaction can comprise derivatizing the conjugated diene functionality in a vitamin D analyte to attach a label to the analyte.

As shown in FIG. 1, the two-step chemical reaction can comprise first treating the vitamin D analyte with a dienophile reagent having an acetyl group, to form a Diels-Alder adduct. The Diels-Alder adduct can then be treated with mass spectrometry (MS) tagging reagent. According to some embodiments, liquid chromatography-tandem mass spectrometry (LC-MS/MS) can be used to analyze the modified analyte. Adducts of different analytes can have different distinct retention times on a reversed phase column, and distinct masses, and can elute from the column at separate times. The eluant from the column can be subjected to MSMS analysis. Under high energy collision, reporter groups can be generated. The intensities or peak areas of the reporter groups can be used for identification and/or quantitation.

According to various embodiments, a plurality of mass spectrometry (MS) tagging reagents is provided for labeling or tagging one or more vitamin D analytes. According to some embodiments, the MS tagging reagents can fragment well to provide intense reporter ions. According to some embodiments, the MS tagging reagents can comprise aminoxy MS tagging reagents that are specifically designed for a Multiple Reaction Monitoring (MRM) assay. According to some embodiments, at least two different categories of aminoxy MS tagging reagents can be used to generate reporter groups under high energy collisions. Exemplary compounds from a first and second category or set of aminoxy MS tagging reagents which can be used, are shown below:

First Category

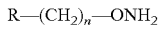

wherein R is

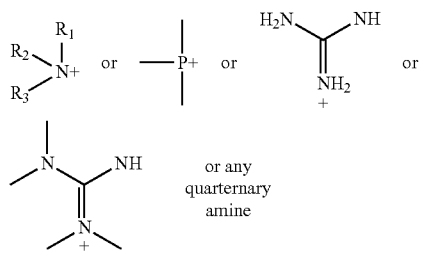

$R_1$, $R_2$, and $R_3$ can each independently be a hydrogen atom or an alkyl group, and n can be from 1 to 20, from 1 to 15, from 1 to 10, or from 1 to 5;

Second Category

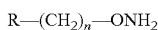

wherein R can be, but is not limited to, one or more of these five structures

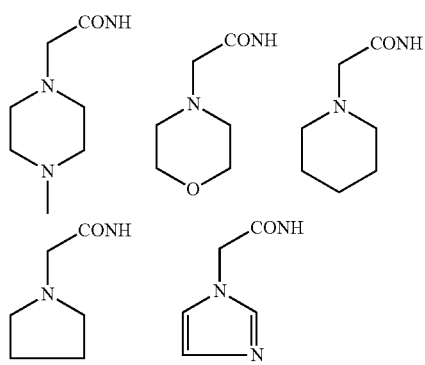

and n can be from 1 to 20, from 1 to 15, from 1 to 10, or from 1 to 5.

Figure 3A:
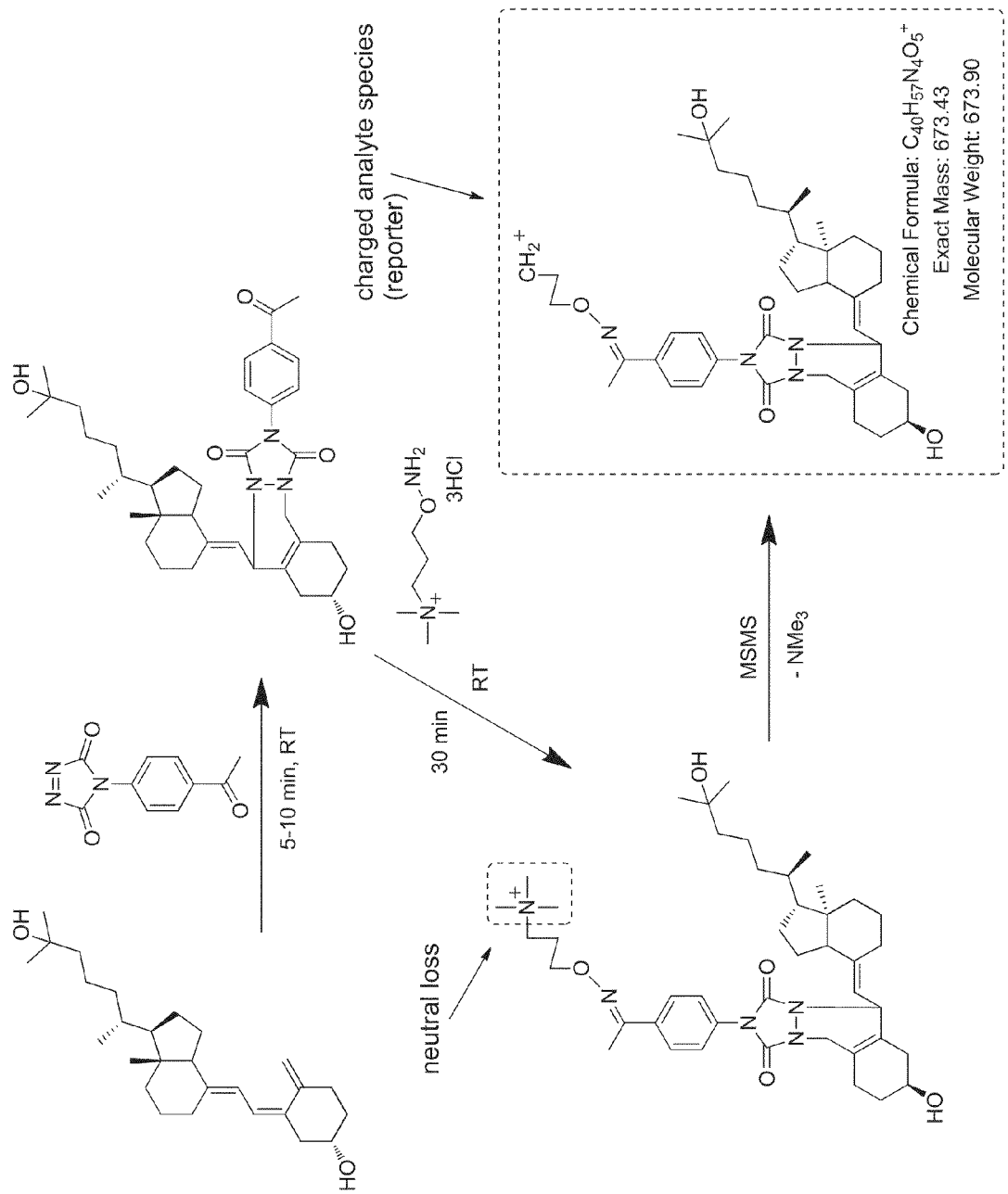
FIG. 3A is a reaction scheme showing fragmentation patterns for generating reporter ions for monohydroxy vitamin D3 using an aminoxy reagent that leaves a charged analyte species as the reporter ion, according to various embodiments of the present teachings.
Figure 3B:
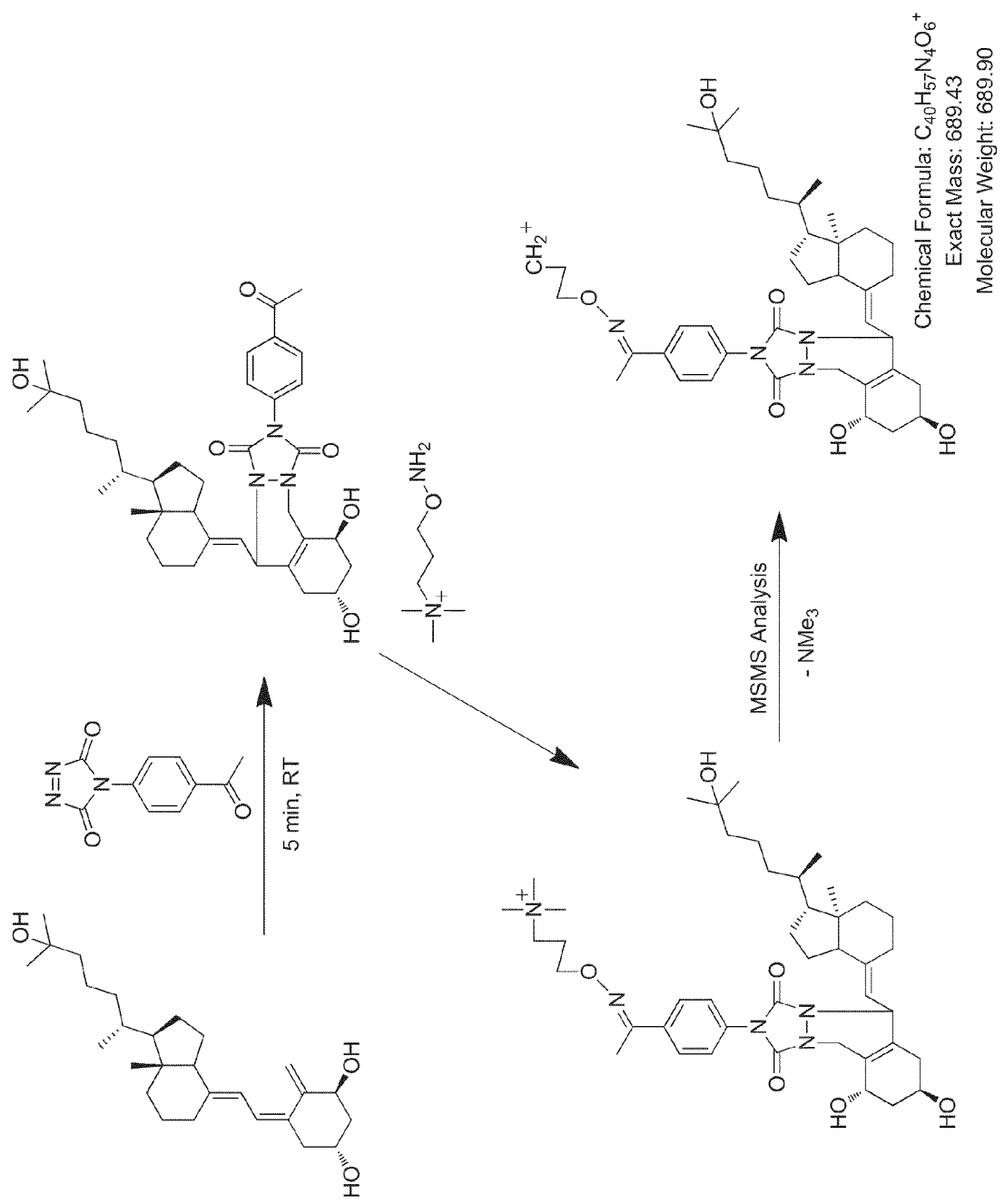
FIG. 3B is a reaction scheme showing fragmentation patterns for generating reporter ions for dihydroxy vitamin D3 using an aminoxy reagent that leaves a charged analyte species as the reporter ion, according to various embodiments of the present teachings.
Figure 3C:
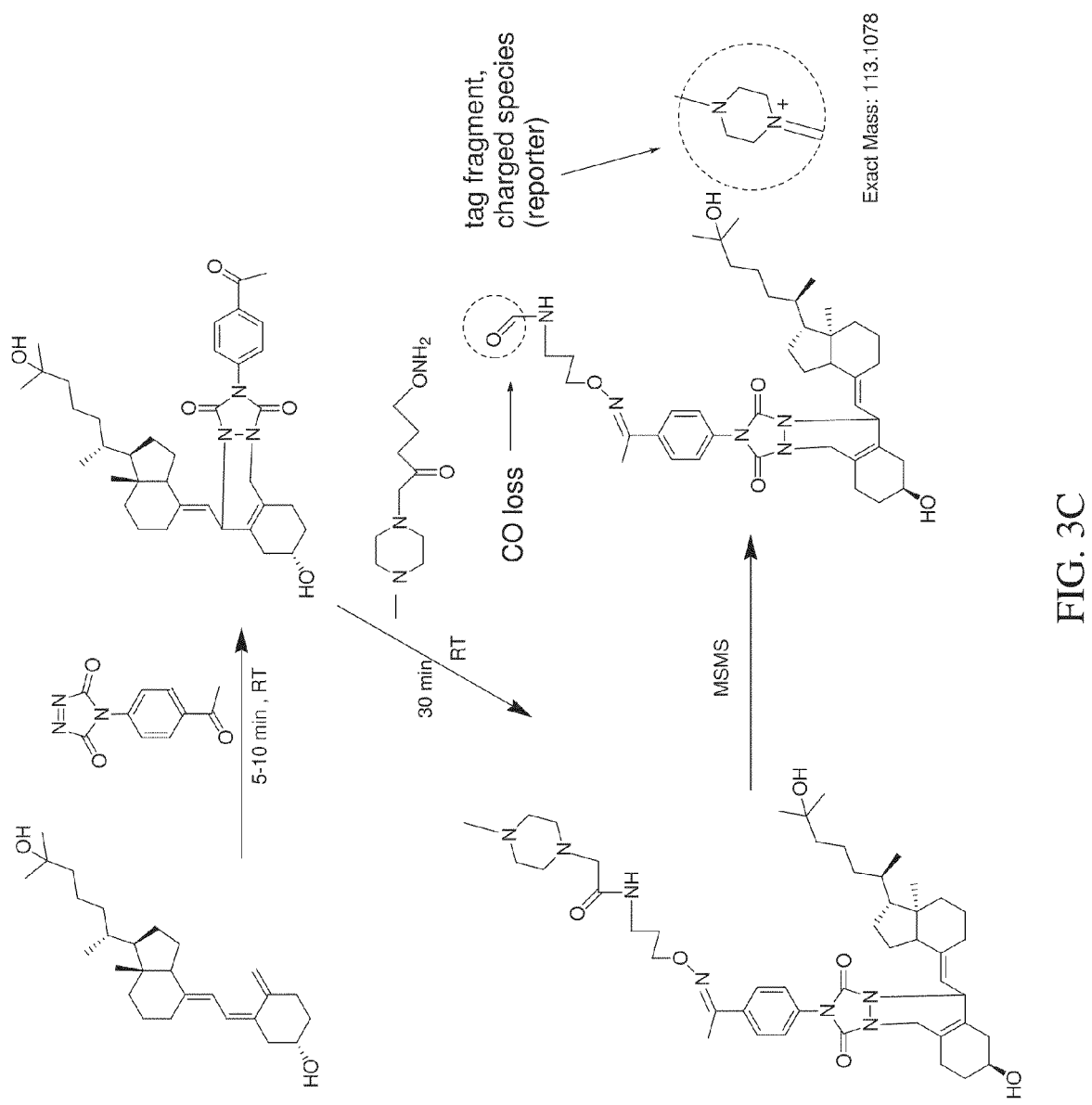
FIG. 3C is a reaction scheme showing fragmentation patterns for generating reporter ions for monohydroxy vitamin D3 using an aminoxy reagent that yields a tag fragment as the reporter ion, according to various embodiments of the present teachings.

As shown in FIGS. 3A and 3B, an aminoxy MS tagging reagent from the first category of aminoxy MS tagging reagents can undergo neutral loss during high energy collision (MSMS) leaving a charged analyte species as the reporter ion, which can then be subjected to $MS^3$ analysis. The vitamin D analyte shown in FIG. 3A is monohydroxy vitamin D3. The vitamin D analyte shown in FIG. 3B is dihydroxy vitamin D3. An aminoxy MS tagging reagent from the second category of aminoxy MS tagging reagents can yield a tag fragment as the reporter ion, on high energy collision, as illustrated in FIG. 3C. The vitamin D analyte shown in FIG. 3C is monohydroxy vitamin D3.

Figure 2B:
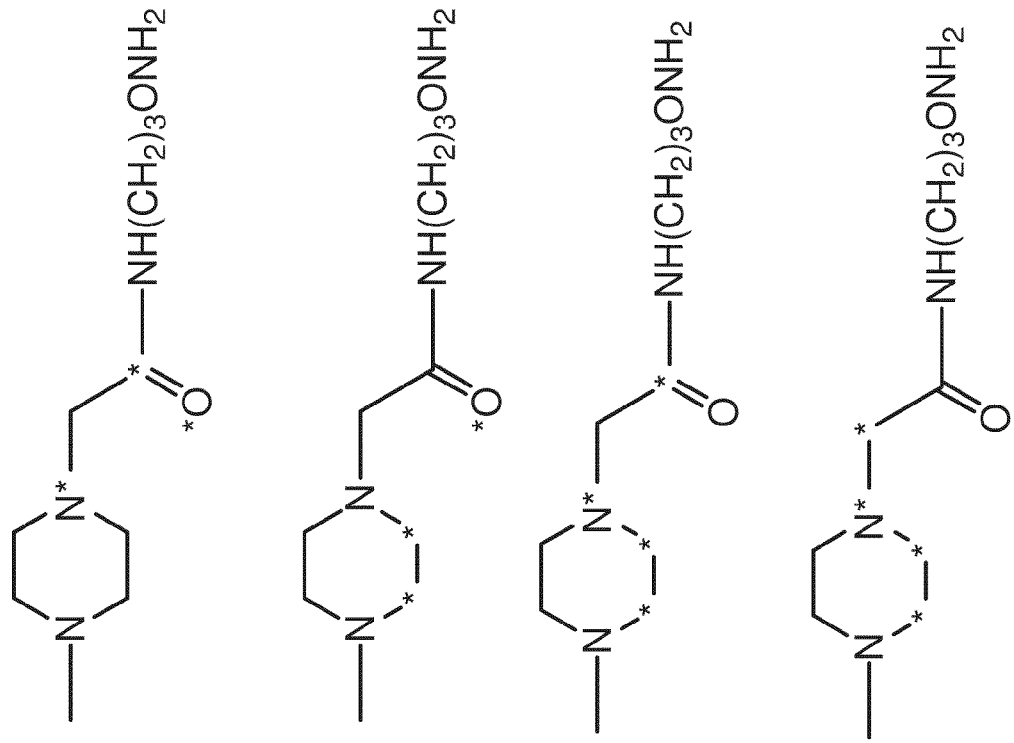
FIG. 2B shows an exemplary set of four aminoxy tagging reagents that can be used in a four-plex assay according to various embodiments of the present teachings.
Figure 2A:
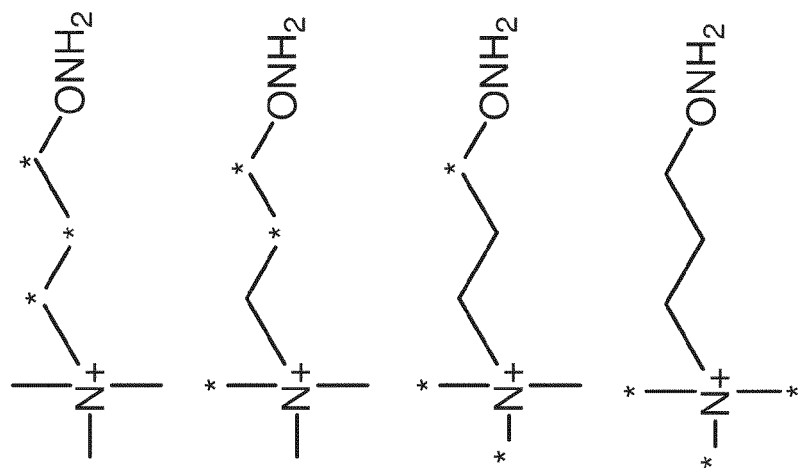
FIG. 2A shows an exemplary set of four aminoxy tagging reagents that can be used in a four-plex assay according to various embodiments of the present teachings.

According to various embodiments, for each type of aminoxy MS tagging reagent, a plurality of isobaric tagging or mass differential tagging reagents can be formulated and used. FIGS. 2A and 2B each respectively depicts a set of isobaric 4-plex aminoxy MS tagging reagents. Each set of isobaric tagging reagents can have identical chemical structures and masses but can comprise different combinations and/or positions of isotopes.

According to various embodiments, a first isobaric tag from one set of isobaric reagents can be made to contact a standard that can comprise a known vitamin D analyte, for example, at a known concentration. The contact can be made under conditions that favor a reaction between the first isobaric tag and the standard. A second isobaric tag from the same set of isobaric reagents as the first isobaric tag can be made to contact a sample comprising an unknown concentration of a vitamin D analyte. As described further below, the tagged analytes of the standard and sample can be mixed together and analyzed to determine the concentration of the analytes in the sample. The analysis can comprise separating the mixture to form separated analytes, and analyzing the separated analytes. Methods of separation that can be used include gas chromatographic methods, liquid chromatographic methods, other chromatographic methods, electrophoretic methods, electroosmotic methods, mass differential separation methods, and the like. In an exemplary embodiment, liquid chromatography is used to separate the various analytes in the mixture and thus form separated analytes.

In some embodiments, chromatographic separation can be preformed on a reversed phase column and peaks eluting from the column can be subject to subsequent analysis. In some embodiments, the subsequent analysis can comprise mass spectrometry or, more particularly, Parent Daughter Ion Transition Monitoring (PDITM). By comparing the results from the PDITM, the concentration of the vitamin D analyte in the sample can be determined, as is described in more detail below. More details about PDITM and its use can be found in published application US 2006/0183238 A1, which is incorporated herein in its entirety by reference.

Figure 5:
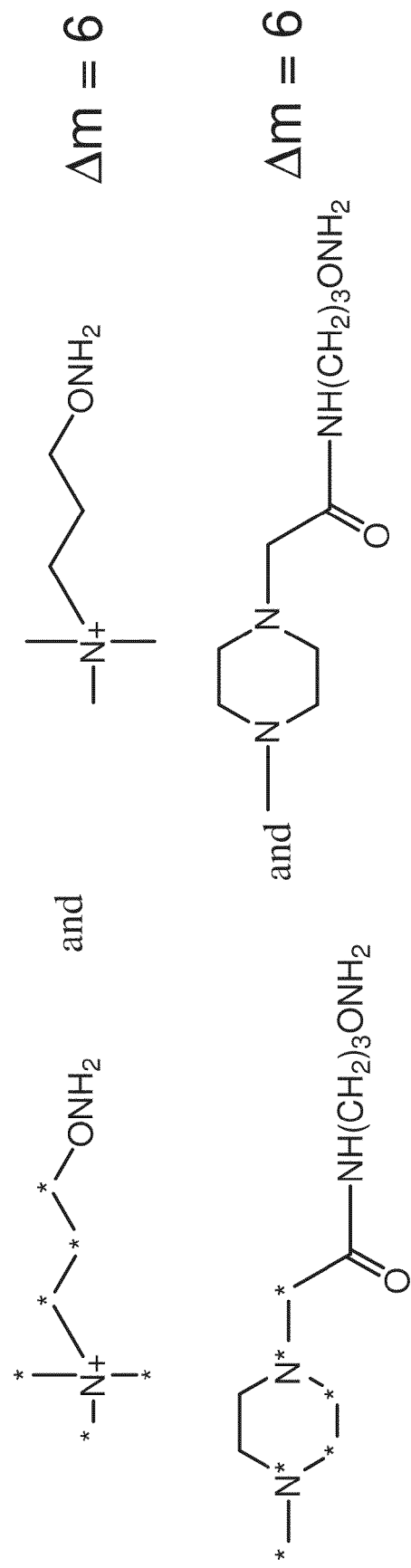
FIG. 5 shows two exemplary mass differential reagent pairs according to various embodiments of the present teachings.

According to some embodiments, mass differential tagging reagents instead of isobaric tagging reagents, can be used. Exemplary mass differential reagent pairs are depicted in FIG. 5. According to various embodiments, the aminoxy MS tagging reagents can be used for relative and absolute quantitation in multiplex assays. According to some embodiments, the aminoxy MS tagging reagents can be used for two-plex, three-plex, four-plex, and other multi-plex assays.

Figure 4A:
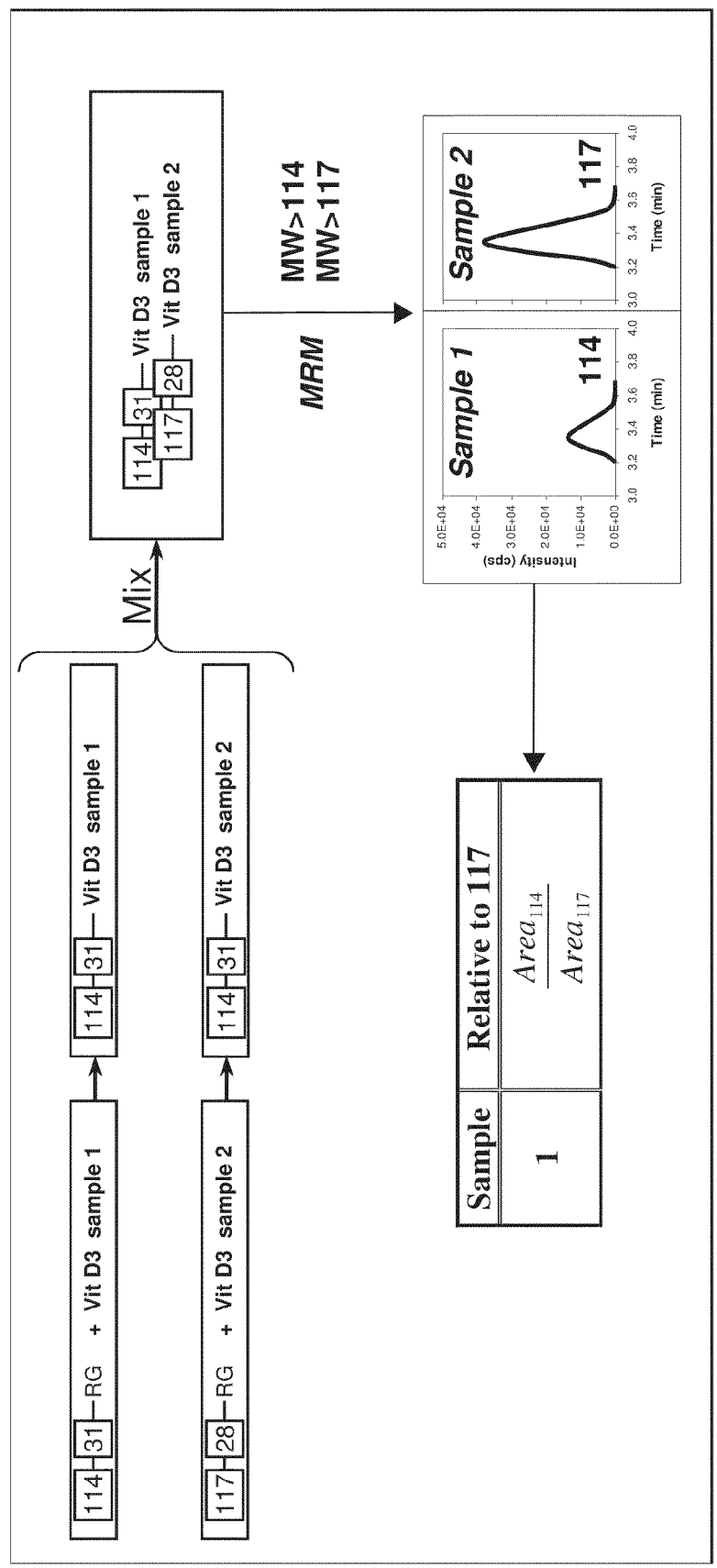
FIG. 4A is a schematic flow diagram showing the various steps involved with relative quantitation in a two-plex assay according to various embodiments of the present teachings.
Figure 4B:
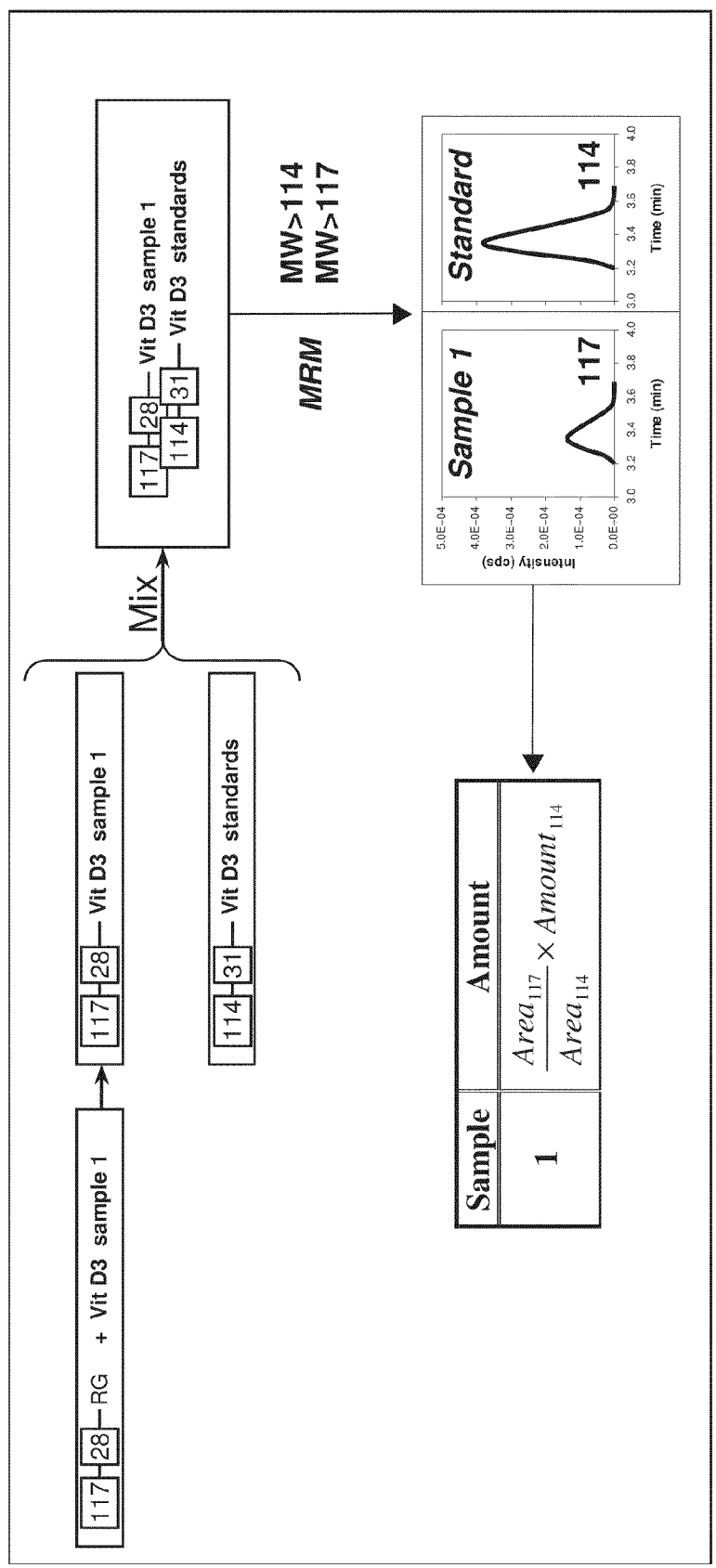
FIG. 4B is a schematic flow diagram showing the various steps involved with absolute quantitation in a two-plex assay according to various embodiments of the present teachings.

An exemplary method of quantitation is shown with reference to FIGS. 4A and 4B, which illustrate relative and absolute quantitation for a two-plex assay, respectively. As described in FIG. 4A, the method can begin with labeling a first sample containing a known vitamin D analyte. The first sample can be, for example, a standard containing a known concentration of a known vitamin D analyte (FIG. 4B). The first sample can be labeled with a first isobaric tag from a set of isobaric tags. Next, a second sample having an unknown analyte in an unknown concentration can be labeled with a second isobaric tag from the same set of isobaric tags. The labeled first sample can then be combined with the labeled second sample to form a mixture. Subsequently, the mixture can be subjected to separation, such as liquid chromatography (LC) separation, for example, on a reversed phase column. The labeled analytes can elute from the column at separate times due to their different and distinct retention times on the column. The peaks eluted from the reversed phase column comprise peaks that contain the labeled analytes from the first sample and peaks that contain the labeled analytes from the second sample. Next, each peak eluted from the column can be subjected to Parent Daughter Ion Transition Monitoring (PDITM). The ratio of the signal intensity of peak area of the reporter signals generated from the first sample, relative to those generated from the second sample, gives the relative concentration of the analyte in the test sample, as shown in FIG. 4A. When the concentration of the labeled standard is known, the specific concentration of the analyte in the sample can be determined, as shown in FIG. 4B.

Figure 4C:
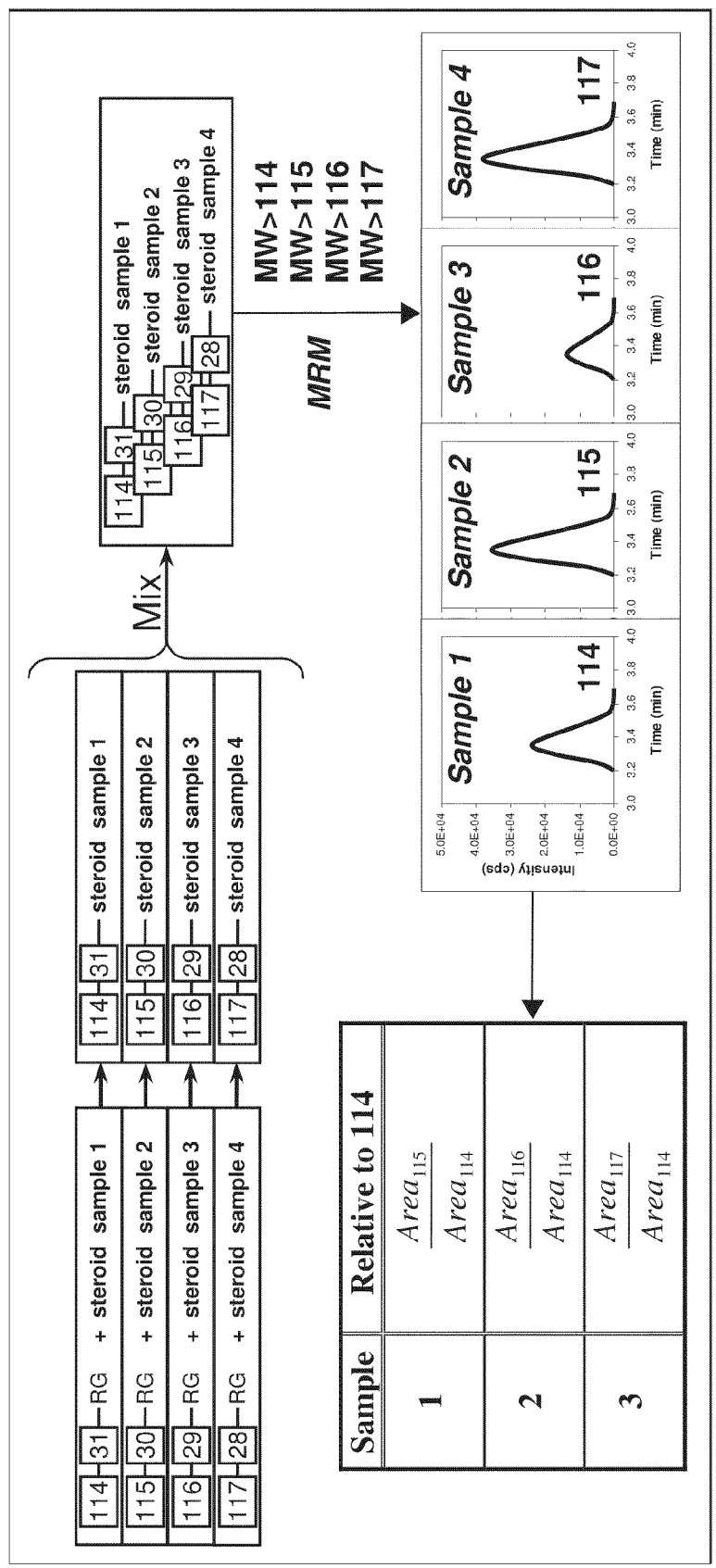
FIG. 4C is a schematic flow diagram showing the various steps involved with relative quantitation in a four-plex assay according to various embodiments of the present teachings.
Figure 4D:
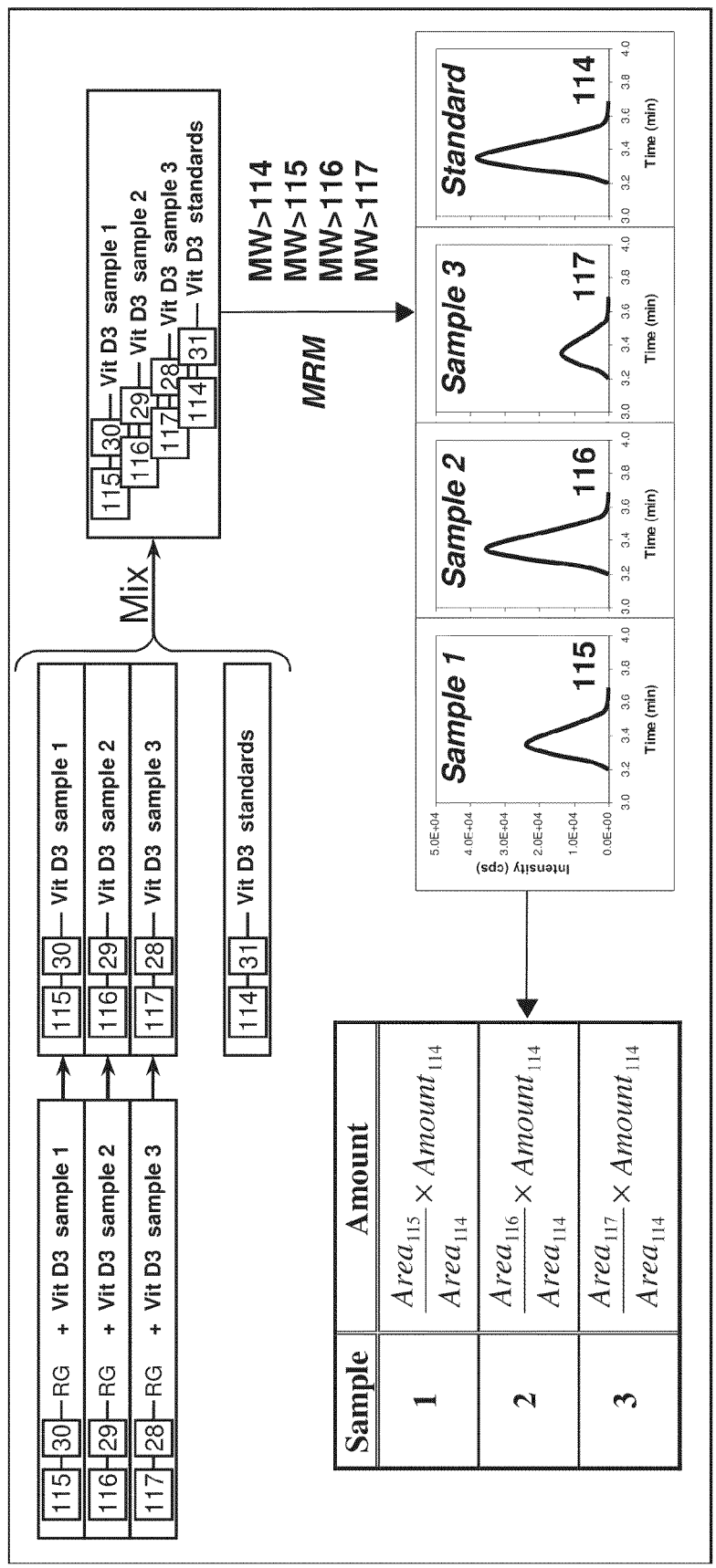
FIG. 4D is a schematic flow diagram showing the various steps involved with absolute quantitation in a four-plex assay according to various embodiments of the present teachings.

Another exemplary method of relative and absolute quantitation is shown with reference to FIGS. 4C and 4D, which illustrate relative and absolute quantitation for a four-plex assay, respectively. As described in FIG. 4C, the method can begin with labeling four samples with first, second, third, and fourth isobaric tags, respectively, that are from the same set of isobaric tags. One of the samples can be a standard having a known concentration of a known vitamin D analyte, as depicted in FIG. 4D. The labeled samples can be combined to form a mixture. Subsequently, the mixture can be subjected to separation, such as liquid chromatography (LC) separation, for example, on a reversed phase column. The labeled analytes can be eluted from the column at separate times due to their different and distinct retention times on the column. The peaks eluted from the reversed phase column can comprise peaks that contain the labeled analytes and peaks that contain the labeled standard. Next, each peak eluted from the column can be subjected to Parent Daughter Ion Transition Monitoring (PDITM). The ratio of the signal intensity of peak area of the reporter signals generated from the labeled standard, relative to those generated from the labeled test samples, gives the relative concentrations of the analytes in the test samples, as shown in FIG. 4C. When the concentration of the labeled standard is known, the specific concentration of each analyte in each of the samples can be determined, as shown in FIG. 4D.

Figure 6:
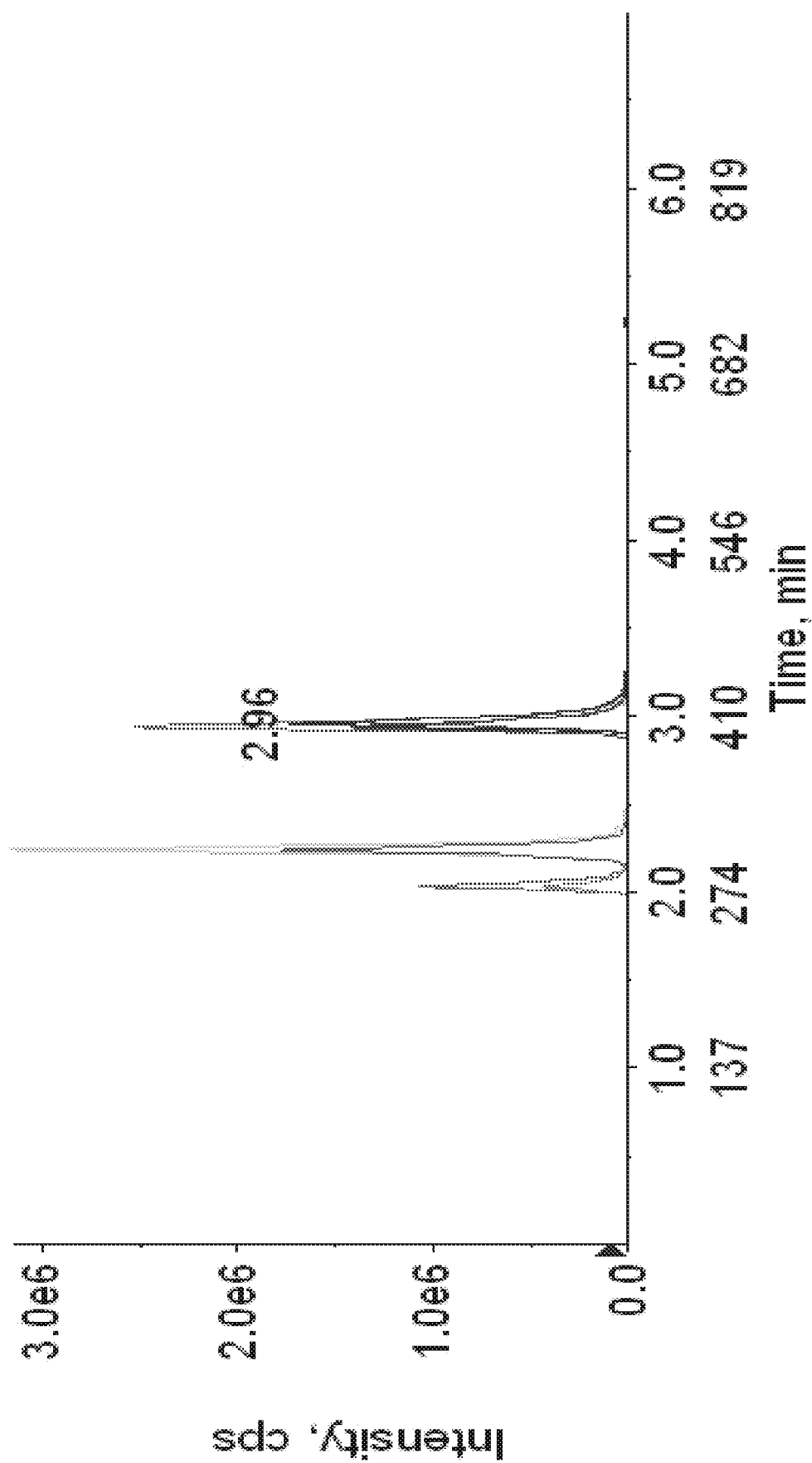
FIG. 6 is a spectrogram showing HPLC separation of labeled analytes according to various embodiments of the present teachings.

According to various embodiments, a method for relative quantitation of one or more vitamin D analytes can comprise labeling the one or more analytes, followed by analysis using mass spectrometry. According to some embodiments the one or more anlaytes can be vitamin D3 and/or metabolites of vitamin D3. According to some embodiments, the method can comprise labeling both a standard sample containing vitamin D3 and/or metabolites of vitamin D3, and a test sample, with MS tagging reagents. According to some embodiments, the MS tagging reagents can be aminoxy tagging reagents. According to some embodiments, the aminoxy tagging reagents can comprise a set of isobaric tags. According to some embodiments, the standard sample can be labeled with a first isobaric tag from a set of isobaric tags, in two steps, as shown in FIG. 1. In the first step, vitamin D analytes in the standard sample can be treated with a dienophile reagent having an acetyl group, to form a Diels-Alder adduct. In the second step, the Diels-Alder adduct can be treated with the first isobaric tag. The test sample can be labeled with a second isobaric tag from the same set of isobaric tags, which is different from the first isobaric tag, in a similar two-step process as is used for the standard sample. The labeled standard sample and the labeled test sample can then be combined and the resulting mixture can be subjected to liquid chromatography (LC) separation on a reversed phase column. The labeled vitamin D3 and/or vitamin D3 metabolites can have distinct retention times and can elute from the column at separate times. The eluting peaks can comprise peaks containing the labeled analyte and peaks containing the labeled standard. FIG. 6 shows HPLC separation of labeled vitamin D3 analytes. The eluant from the column can subsequently be analyzed using mass spectrometry.

Figure 7:
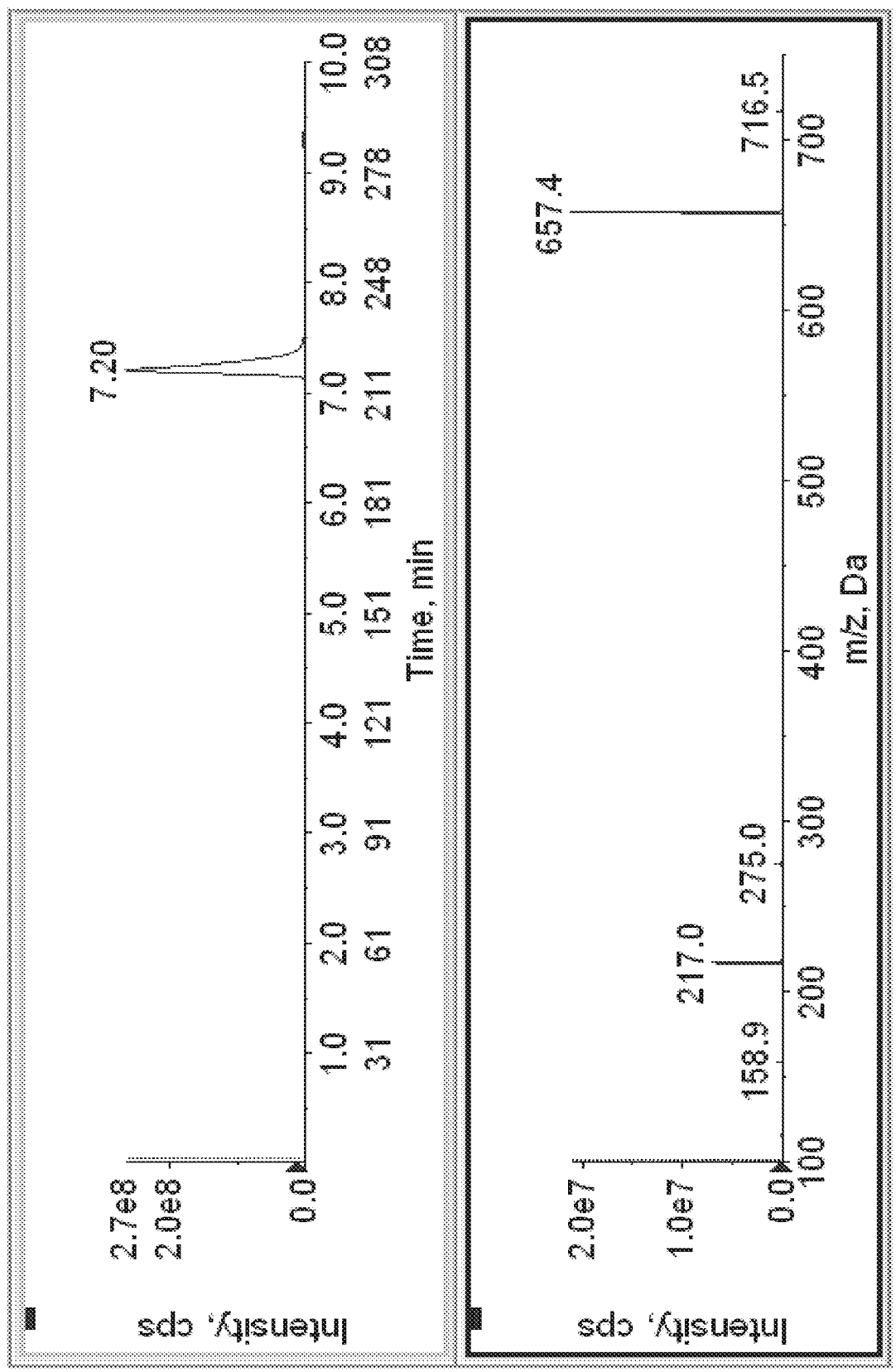
FIG. 7 is an MSMS spectrogram of labeled vitamin D3, obtained according to various embodiments of the present teachings.

FIG. 7 shows a mass spectrogram of labeled vitamin D3 using MSMS. According to some embodiments, when the isobaric tag is an aminoxy MS tagging reagent, the reporter signal can be subjected to further fragmentation ($MS^3$). Subjecting the reporter signal to further fragmentation can provide peaks that enable confirmatory identification of the analyte by comparing with a standard database. According to some embodiments, the eluant from the column can be subjected to Parent Daughter Ion Transition Monitoring (PDITM).

Figure 8:
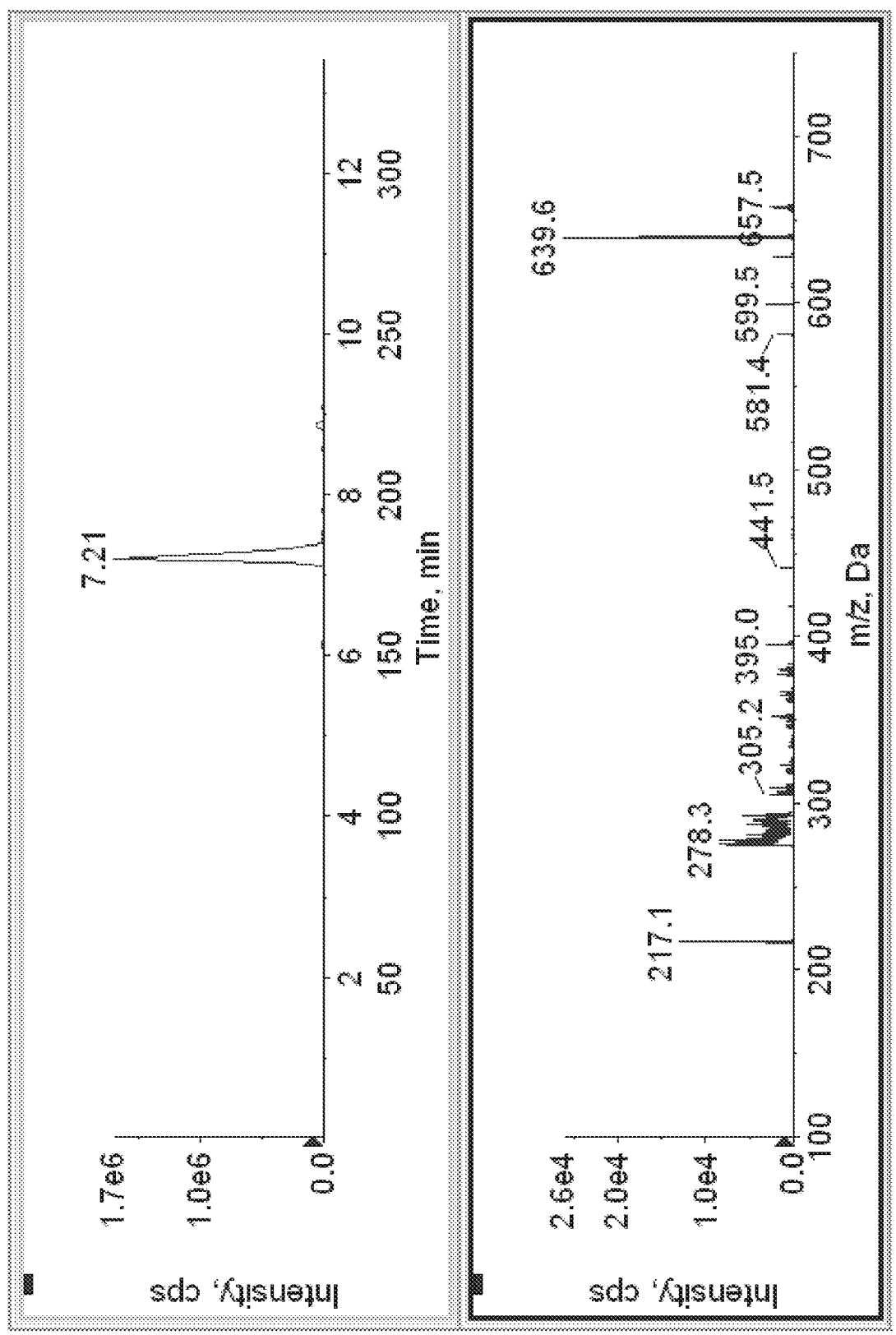
FIG. 8 shows an $MS^3$ spectrogram of labeled vitamin D3, obtained according to various embodiments of the present teachings.
Figure 9:
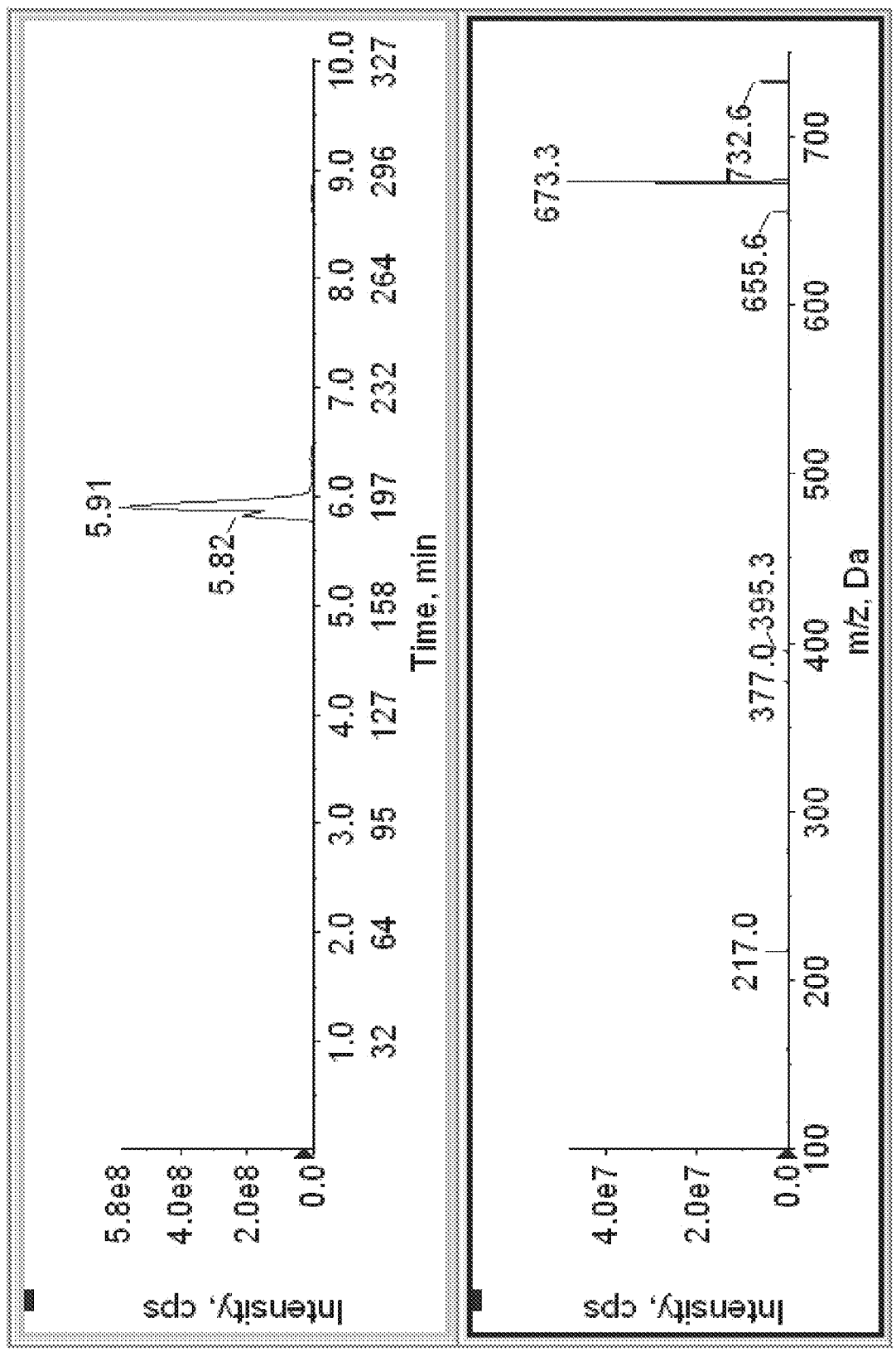
FIG. 9 shows an MSMS spectrogram of labeled monohydroxy vitamin D3, obtained according to various embodiments of the present teachings.
Figure 10:
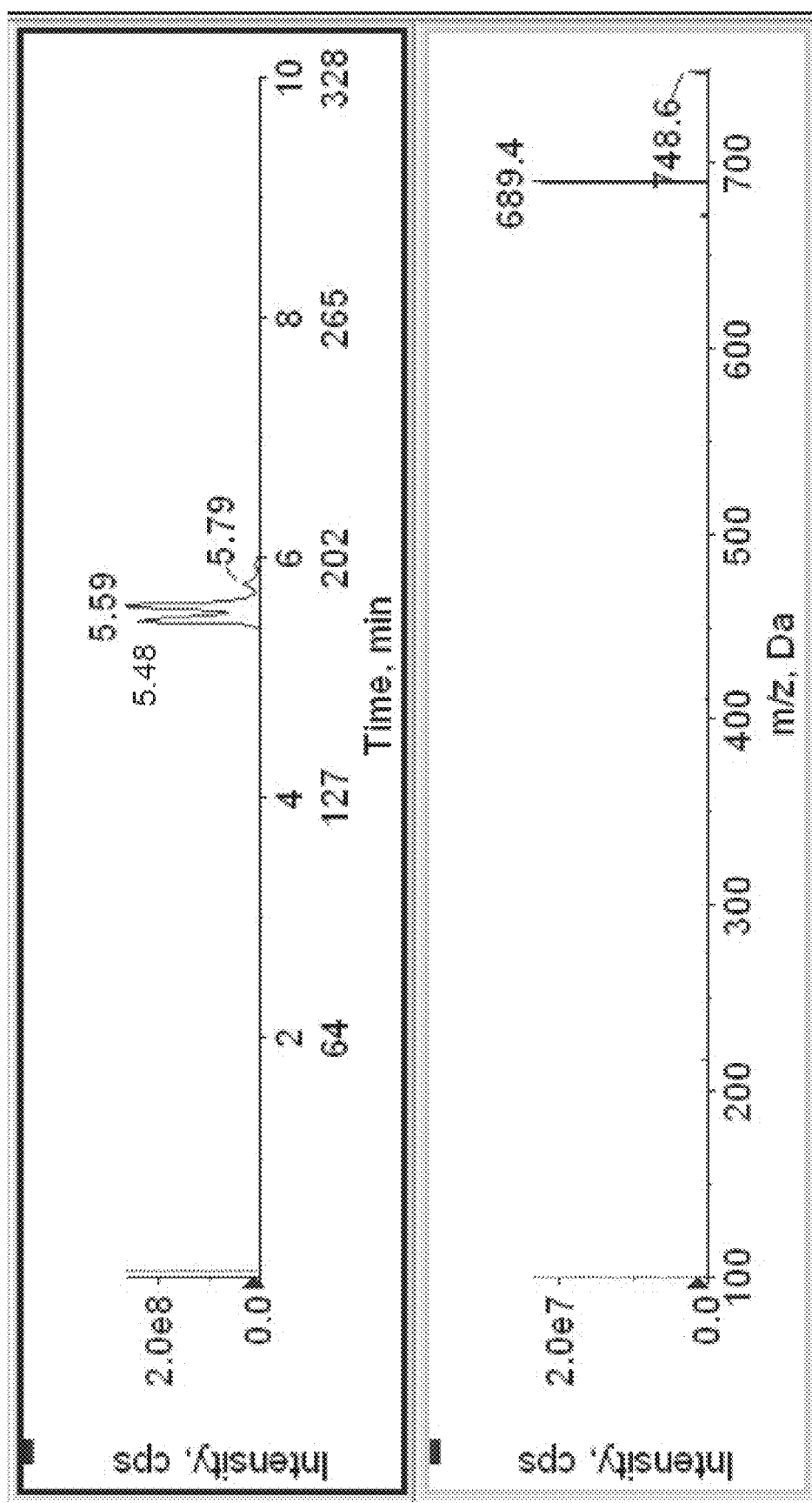
FIG. 10 shows an MSMS spectrogram of labeled dihydroxy vitamin D3, obtained according to various embodiments of the present teachings.

FIG. 8 shows a mass spectrogram of labeled vitamin D3, obtained using $MS^3$. The ratios of the signal intensity or peak area of the reporter signals generated from the standard compared to those generated from the test sample can indicate the concentration of the analyte in the test sample relative to the standard sample.

Figure 11:
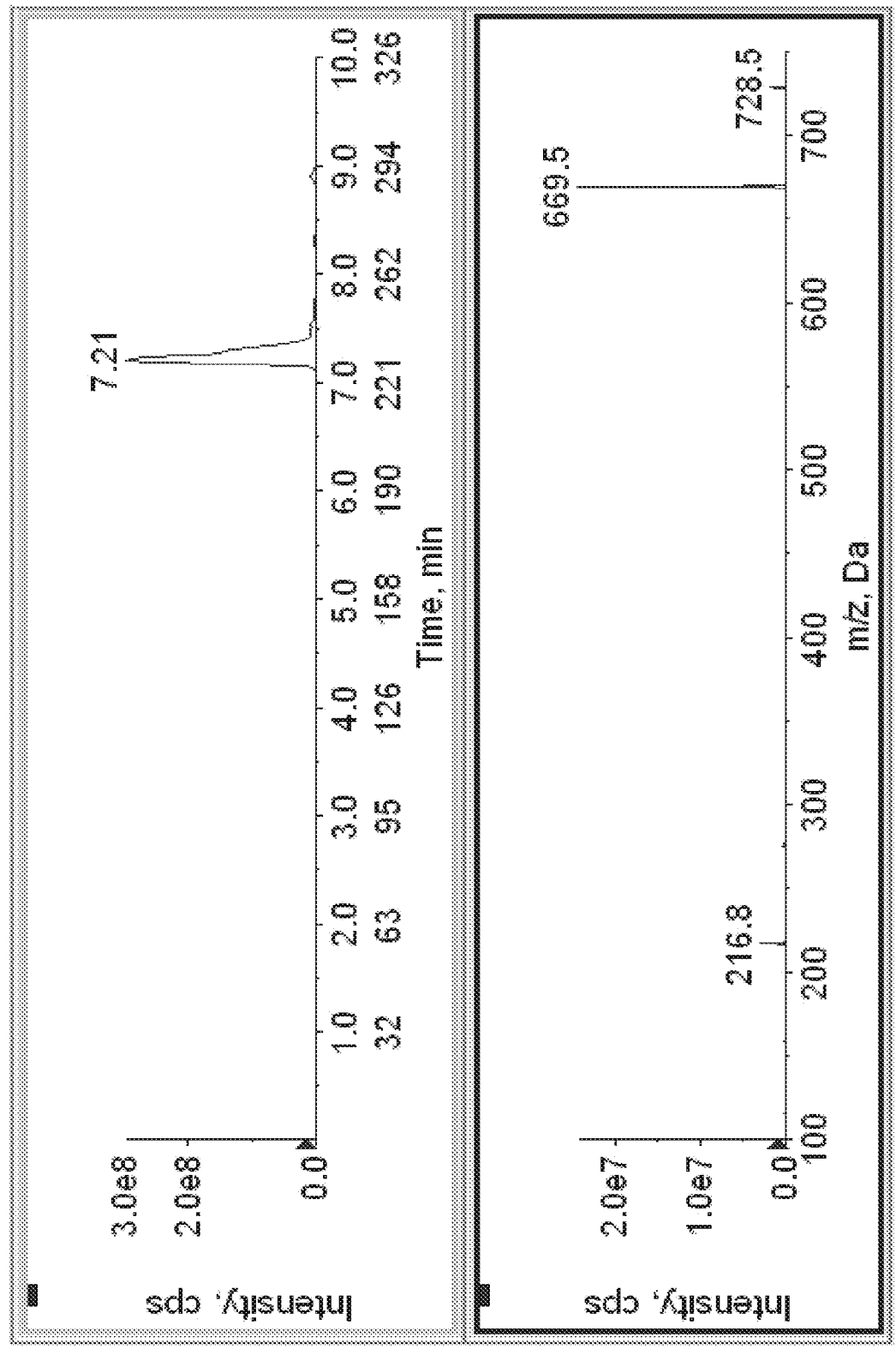
FIG. 11 shows an MSMS spectrogram of labeled vitamin D2, obtained according to various embodiments of the present teachings.

It should be understood that absolute quantitation of vitamin D analytes, where the standard sample has a known concentration of a vitamin D analyte, can be performed in the same manner as described above for relative quantitation. Also, where vitamin D3 and/or metabolites of vitamin D3 are mentioned above, it should be understood that any vitamin D analyte can be used. FIG. 11, for example, shows an MSMS spectrogram of vitamin D2 that has been labeled in accordance with the present teachings.

The tagging chemistry and the methodology of the present teachings provide increased sensitivity relative to known methods, and eliminate the need for $^2$H-containing, $^{13}$C-containing, $^{15}$N-containing, and $^{18}$O-containing standards of vitamin D analytes. Isotope labeled standards of some vitamin D analytes are not commercially available, which makes absolute quantitation of these analytes difficult without the present teachings. According to the present teachings, each analyte can have its own internal standard. The reporter signals can be specific to the standard sample and to the test sample.

Isobaric tags allow for multiplexing and provide the only known method to date for multiplexed analysis of vitamin D analytes, and provide high throughput and lower cost of analysis per sample. Since there is one common functional group in all of the vitamin D analytes, only one tag is needed for each analyte, as shown in FIGS. 3A and 3B. In some embodiments, using PDITM increases specificity and reduces the risk of error. The reagent design makes it a good tool for FlashQuant™ application and enables $MS^3$ capability which helps in confirming the identity of the analyte.

Figure 14:
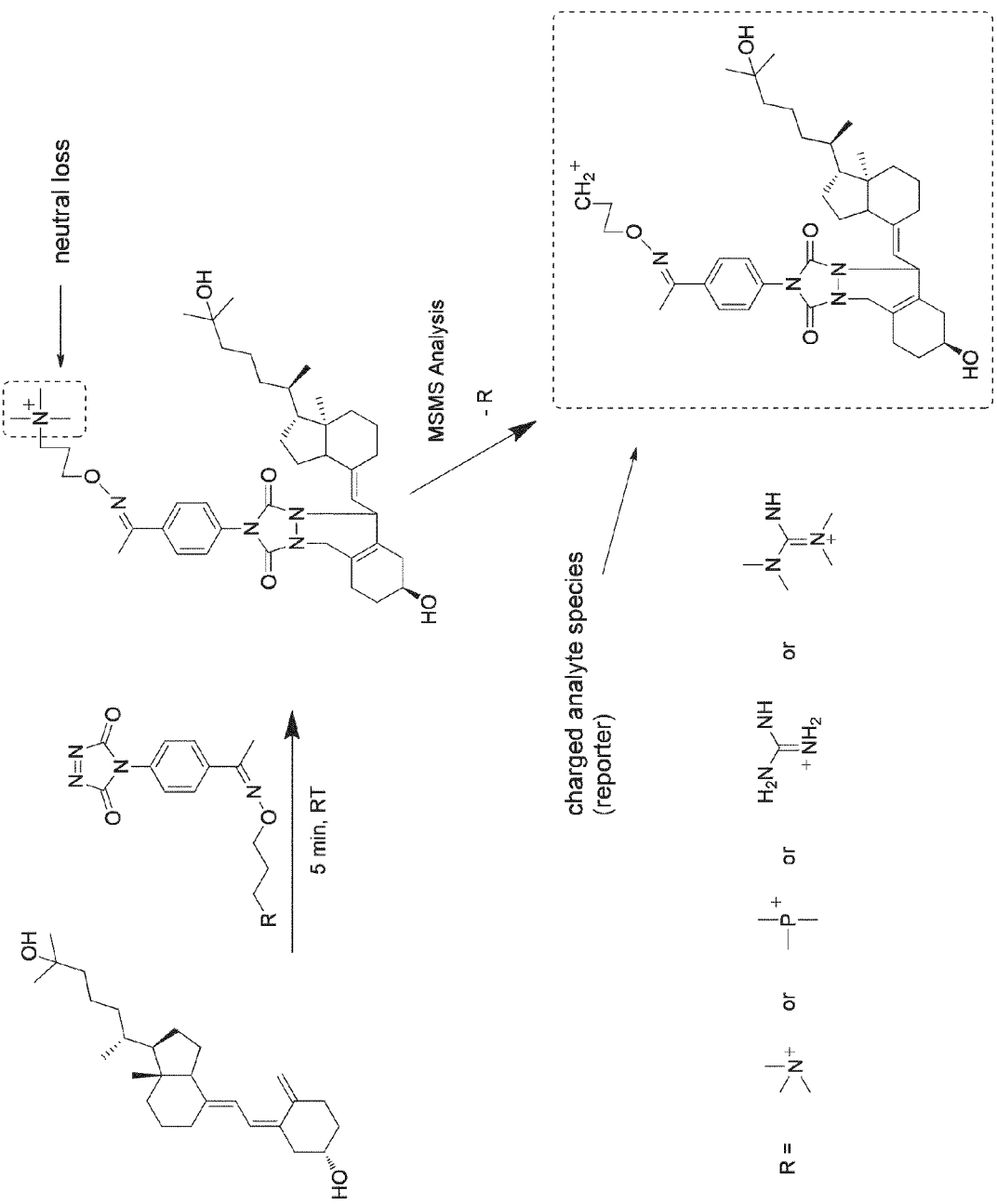
FIG. 14 shows a reaction scheme for a one-step chemical reaction, exemplary substituents that can be used for the tagging molecule, and an MSMS workflow, that can be used to label and quantify vitamin D analytes according to various embodiments of the present teachings.
Figure 15:
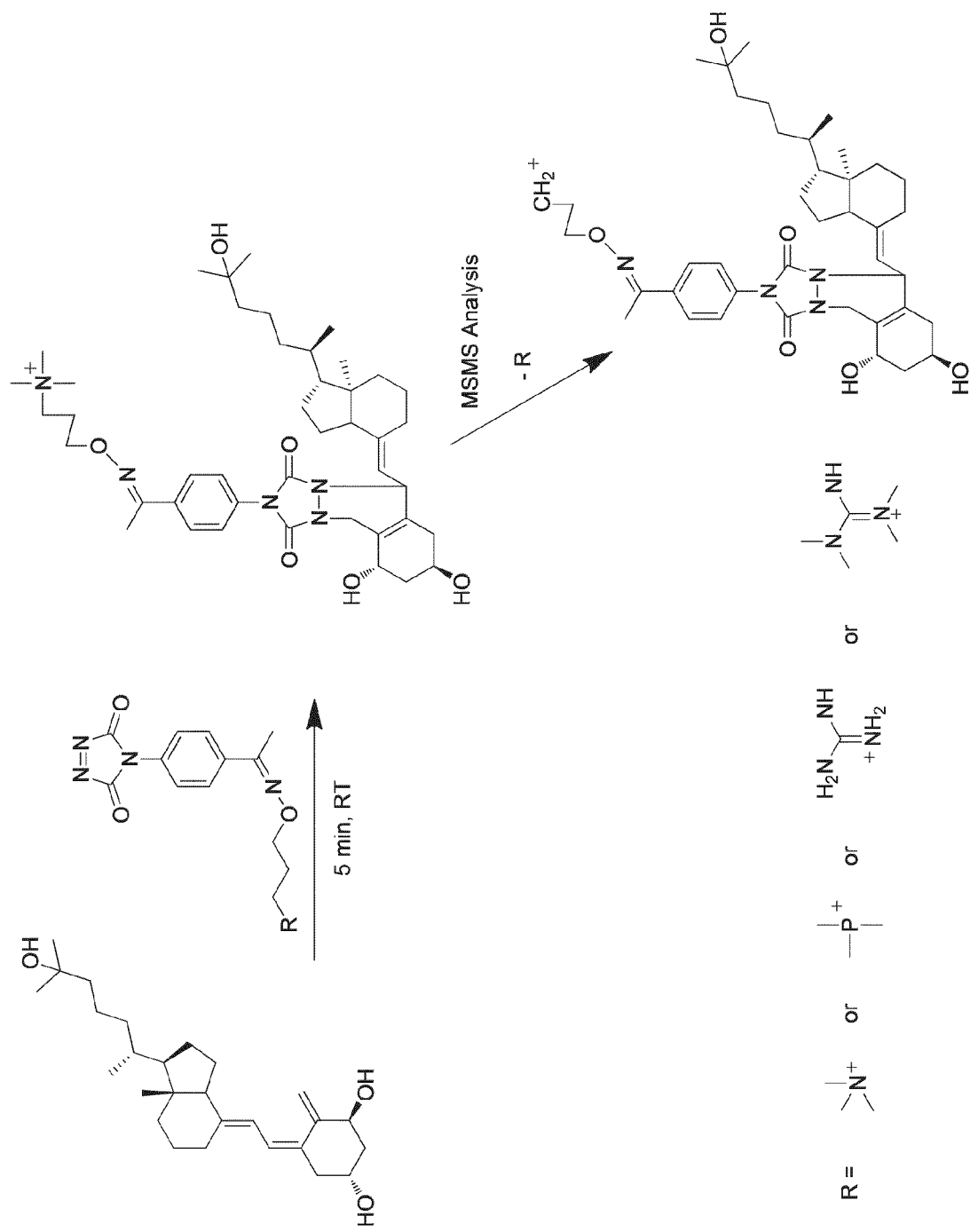
FIG. 15 shows a reaction scheme for a one-step chemical reaction, exemplary substituents that can be used for the tagging molecule, and an MSMS workflow, that can be used to label and quantify dihydroxy vitamin D3 analyte, according to various embodiments of the present teachings.

According to various embodiments, a method for quantitating a vitamin D analyte in a sample is provided, wherein the method comprises tagging a vitamin D analyte with a one-step tagging reagent, for example, a Diels-Alder adduct. The product can then be analyzed using mass spectrometry. According to various embodiments, the tagging reagent can comprise a compound having the structure shown in FIG. 12A. Under high energy collision, a reporter group is generated. The intensity or the peak area of the reporter group is used for quantitation. The one-step tagging reagents shown in FIG. 12A undergo neutral loss during high energy collision (MSMS) leaving a charged analyte species as the reporter ion, such as shown in FIGS. 14 and 15, and the reporter ion can then be subjected to $MS^3$ analysis.

Figure 16:
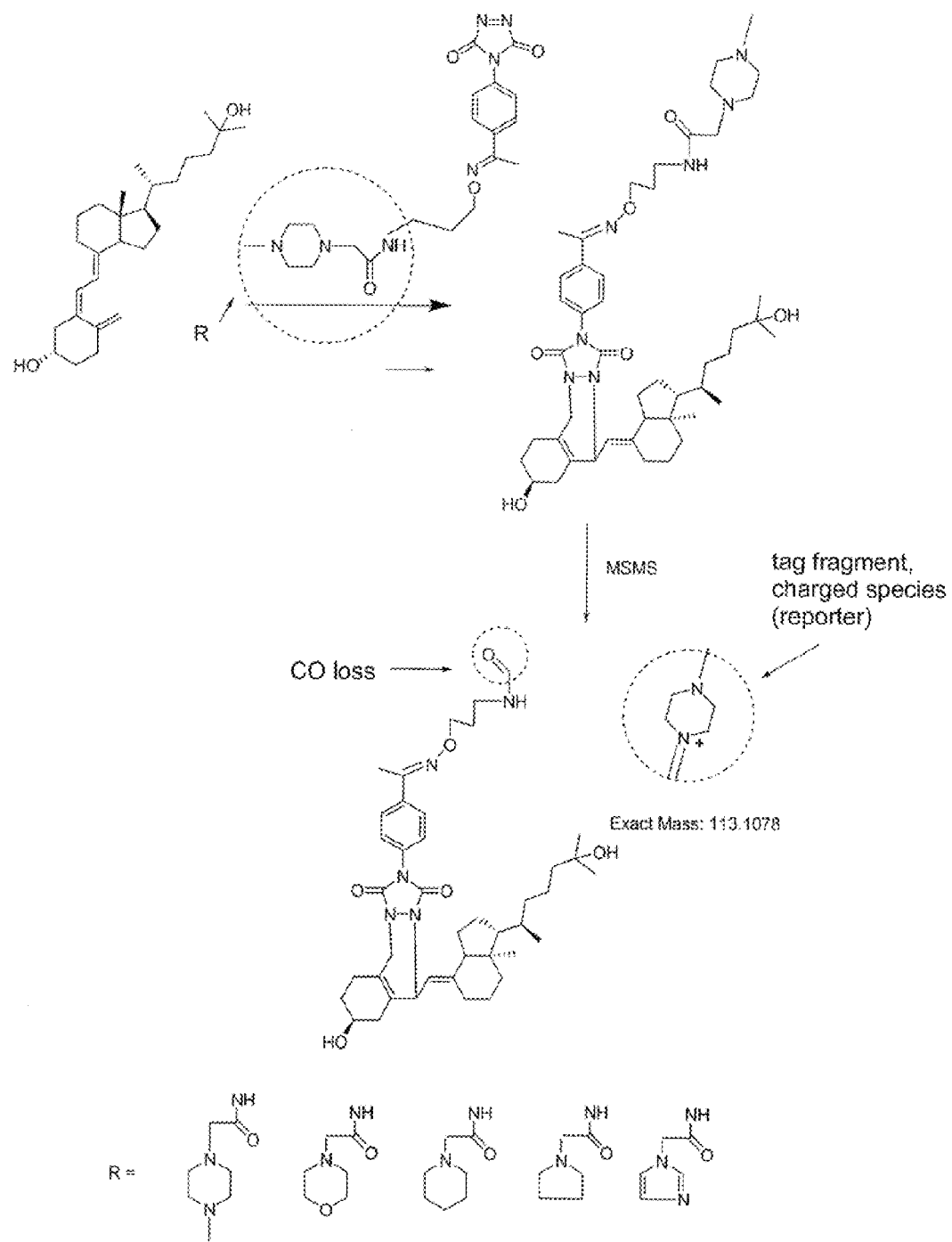
FIG. 16 shows a reaction scheme for a one-step chemical reaction, exemplary substituents that can be used for the tagging molecule, and an MSMS workflow, that can be used to label and quantify monohydroxy vitamin D analytes according to various embodiments of the present teachings.

In some embodiments, the tagging reagent can comprise a compound having the structure shown in FIG. 12B. The one-step tagging reagents shown in FIG. 12B generate a tag fragment upon high energy collision, such as shown in FIG. 16, and the reporter ion can then be subjected to $MS^3$ analysis.

The method can further comprise providing a standard comprising a known concentration of a known vitamin D analyte and tagging the known vitamin D analyte of the standard with a one-step tagging reagent according to the present teachings, to form a labeled standard. The labeled standard can then be mixed with the labeled sample to form a mixture. The mixture can then be separated to form separated labeled analytes, and the separated analytes can be analyzed.

In some embodiments, the one-step reagent used for the labeled standard can comprise a first isobaric tag from a set of isobaric tags. The labeled sample can comprise a second isobaric tag from the same set of isobaric tags, but that differs from the first isobaric tag. The labeled sample can then be analyzed using mass spectrometry, LC-MSMS analysis of the labeled sample, a combination thereof, or the like.

In some embodiments, the one-step reagent used for the labeled standard can comprise a first mass differential tag from a set of mass differential tags. The labeled sample can comprise a second mass differential tag from the same set of mass differential tags, but that differs from the first mass differential tag. The labeled sample can then be analyzed using mass spectrometry, LC-MSMS analysis of the labeled sample, a combination thereof, or the like.

In some embodiments, parent daughter ion transition monitoring (PDITM) of the labeled analytes is performed using a triple quadrupole MS platform. More details about PDITM and its use are described in U.S. Patent Application Publication No. US 2006/0183238 A1, which is incorporated herein in its entirety by reference. As mentioned above, in some embodiments, the one-step tagging reagent undergoes neutral loss during MSMS and leaves a reporter ion that is a charged analyte species. In some embodiments, the one-step tagging reagent forms a reporter ion that is a tag fragment during MSMS.

According to various embodiments, the vitamin D analyte can comprise a plurality of different vitamin D analytes, and the labeling can comprise labeling each with a plurality of different respective tagging reagents, for example, a different tagging reagent for each different type of analyte. The metabolites to be analyzed and for which a kit can be configured to detect, can comprise analytes of vitamin D2, for example, a monohydroxy metabolite of vitamin D2 and/or a dihydroxy metabolite of vitamin D2. In some embodiments, the metabolites are metabolites of vitamin D3 and can comprise a monohydroxy metabolite of vitamin D3 and/or a dihydroxy metabolite of vitamin D3.

According to various embodiments, the present teachings provide a method for the quantitation of one or more of vitamin D2, vitamin D3, and/or metabolites from the vitamin D family, herein collectively referred to as vitamin D analytes. Vitamin D analytes can include, for example, vitamin D2, vitamin D3, and/or the monohydroxy, dihydroxy and trihydroxy metabolites of vitamin D2 or vitamin D3. According to various embodiments, the method for quantification of one or more vitamin D analytes can comprise a one-step chemical reaction to modify the analytes, followed by mass analysis using mass spectrometry. According to various embodiments, the one-step chemical reaction can comprise derivatizing the conjugated diene functionality in a vitamin D analyte to attach a dienophile-containing tagging reagent to the analyte, to form a Diels-Alder adduct, as exemplified in FIGS. 13-16, which show four different respective reactions using four different one-step tagging reagents, and exemplary substituent groups that can comprise moieties of the respective one-step tagging reagents.

FIG. 17 shows two different sets of exemplary isobaric tags, each set comprising four different reagents that can be used in a four-plex assay, according to various embodiments of the present teachings. In various embodiments, the heavy atom isotopes can be placed in various positions on the molecule.

FIG. 18 shows two different sets of exemplary mass differential tags, each set comprising four different reagents that can be used in a four-plex assay, according to various embodiments of the present teachings. In various embodiments, the heavy atom isotopes can be placed in various positions on the molecule.

Figure 19:
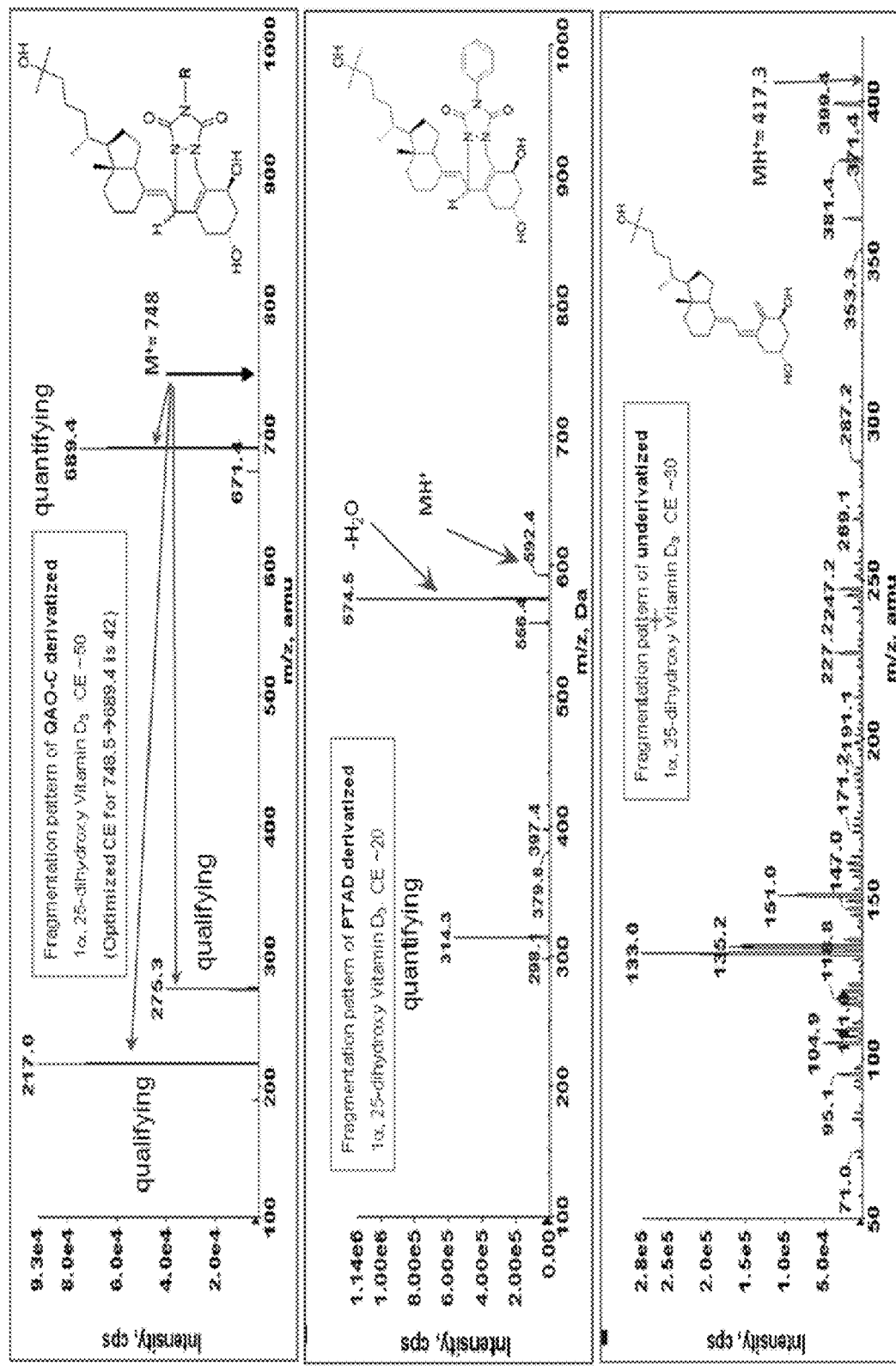
FIG. 19 shows the comparison of QAO-C derivatized 1α,25-DihydroxyVitamin-$D_3$, PTAD 1α,25-DihydroxyVitamin-$D_3$, and underivatized 1α,25-DihydroxyVitamin-$D_3$, according to various embodiments of the present teachings.

FIG. 19 compares the fragmentation pattern of QAO-C derivatized 1α,25-DihydroxyVitamin-D$_3$, PTAD 1α,25-DihydroxyVitamin-D$_3$, (PTAD is a Cookson type reagent); and underivatized 1α,25-DihydroxyVitamin-D$_3$, according to various embodiments of the present teachings. As shown in FIG. 19, the QAO-C derivatized 1α,25-DihydroxyVitamin-D$_3$ produces a clean mass spectrum compared to the spectrum of PTAD 1α,25-DihydroxyVitamin-D$_3$ or that of underivatized 1α,25-DihydroxyVitamin-D$_3$.

FIG. 20 compares the signal intensity of QAO-C derivatized 1α,25-DihydroxyVitamin-D$_3$, PTAD 1α,25-DihydroxyVitamin-D$_3$, and underivatized 1α,25-DihydroxyVitamin-D$_3$, according to various embodiments of the present teachings. As shown in FIG. 20, there is an average of 11 times increase in sensitivity with QAO-C derivatized 1α,25-DihydroxyVitamin-D$_3$ compared to PTAD 1α,25-DihydroxyVitamin-D$_3$ and an average of 192 times increase in sensitivity with the QAO-C derivatized 1α,25-DihydroxyVitamin-D$_3$ compared to underivatized 1α,25-DihydroxyVitamin-D$_3$.

Figure 21:
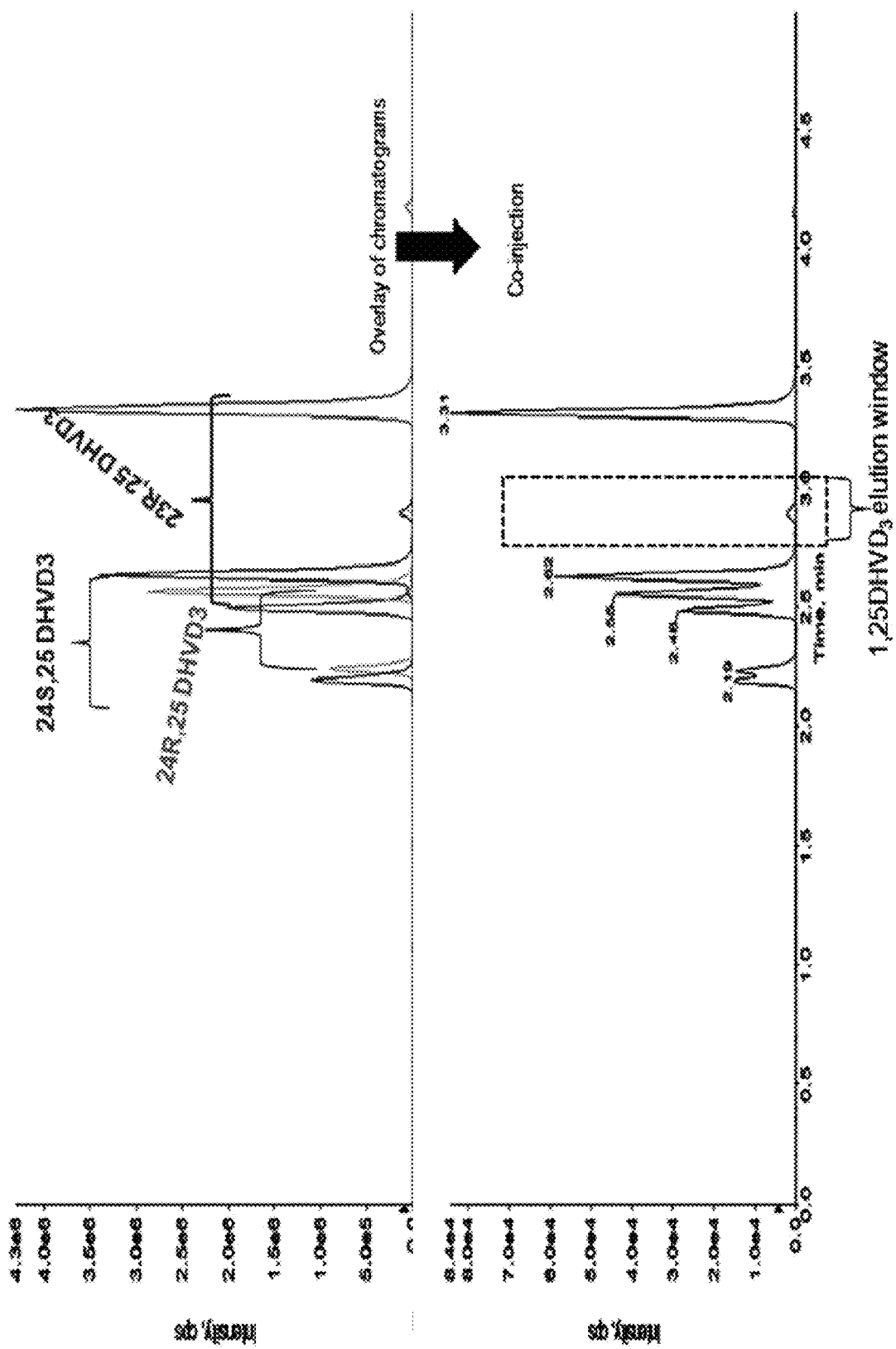
FIG. 21 shows the separation of Vitamin-$D_3$ isomers, according to various embodiments of the present teachings.

FIG. 21 shows isobaric Dihydroxy Vitamin D-3 metabolites being resolved by liquid chromatography. According to various embodiments of the present teachings, as shown in FIG. 21, Vitamin-D$_3$ isomers that otherwise can interfere with 1α,25-DihydroxyVitamin-D$_3$ are separated.

Figure 22:
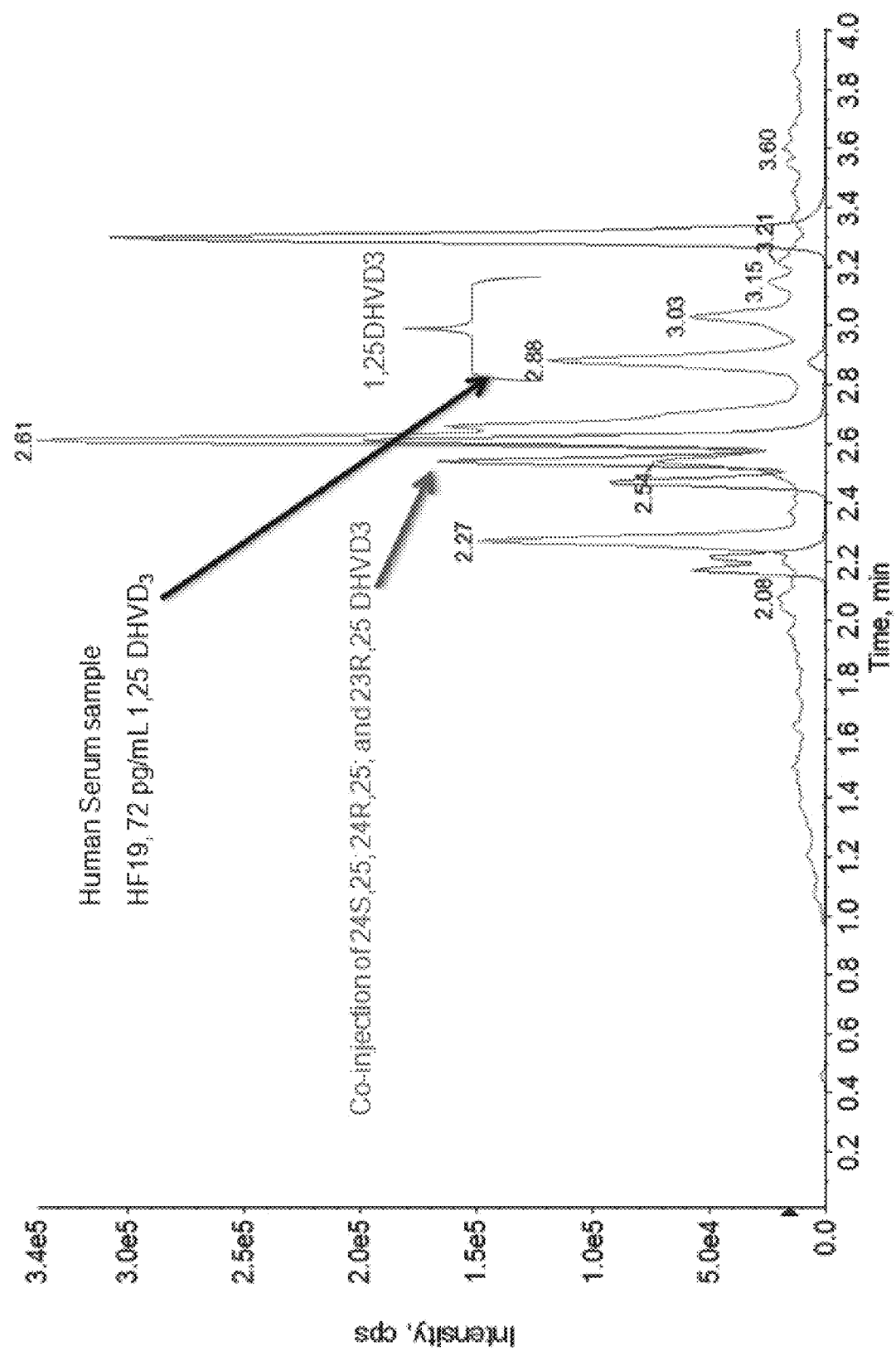
FIG. 22 shows the separation of Vitamin-$D_3$ isomers from 1α,25-DihydroxyVitamin-$D_3$ in human serum sample, according to various embodiments of the present teachings.

FIG. 22 shows the separation of 1α,25-DihydroxyVitamin-D$_3$ from Vitamin-D$_3$ isomers in human serum sample, according to various embodiments of the present teachings.

Figure 23:
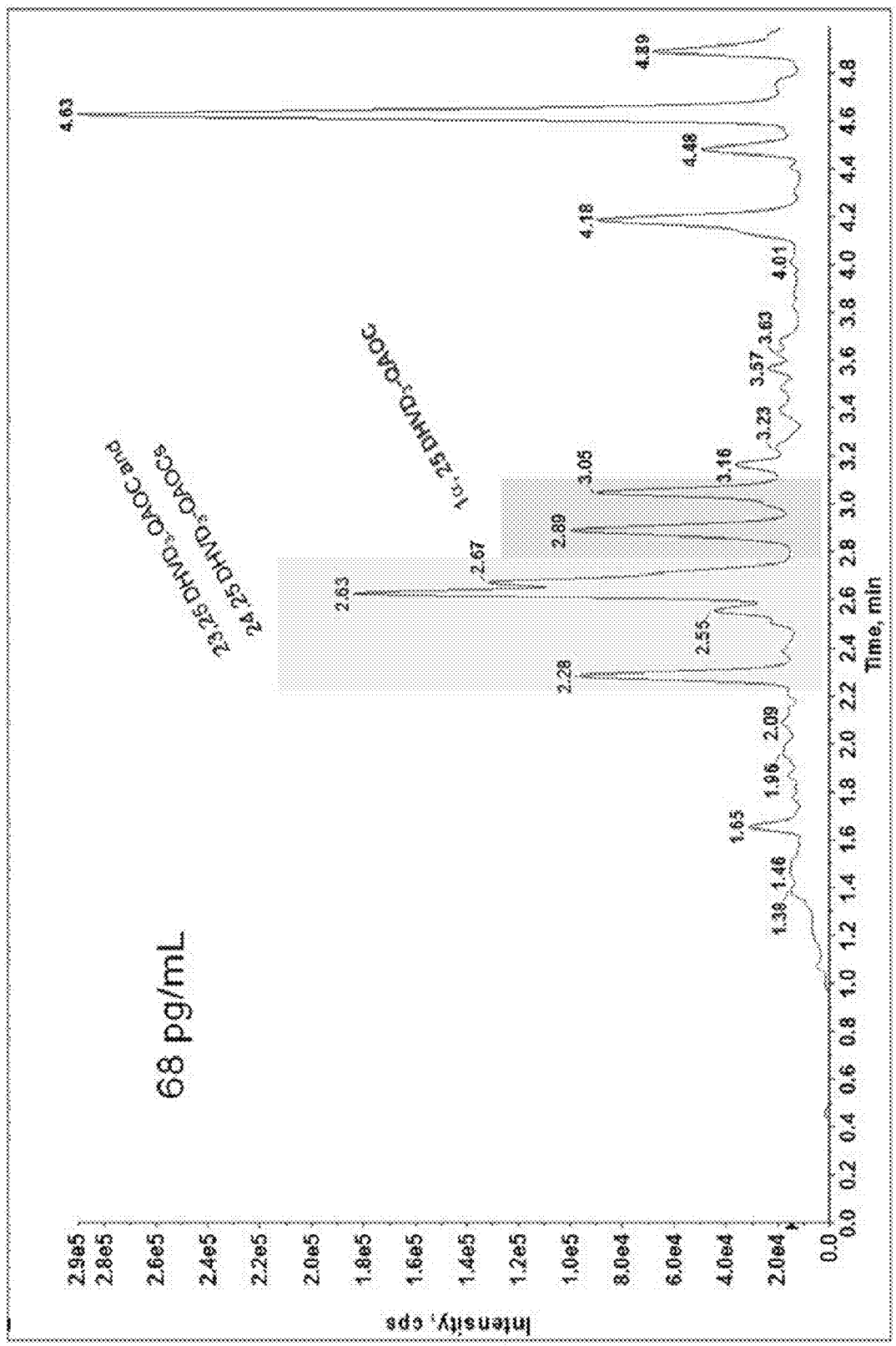
FIG. 23 shows the separation of Vitamin-$D_3$ isomers from 1α,25-DihydroxyVitamin-$D_3$ in an analysis of human serum sample, according to various embodiments of the present teachings.

FIG. 23 shows the separation of 1α,25-DihydroxyVitamin-D$_3$ from Vitamin-D$_3$ isomers in an analysis of human serum sample, according to various embodiments of the present teachings.

Figure 24:
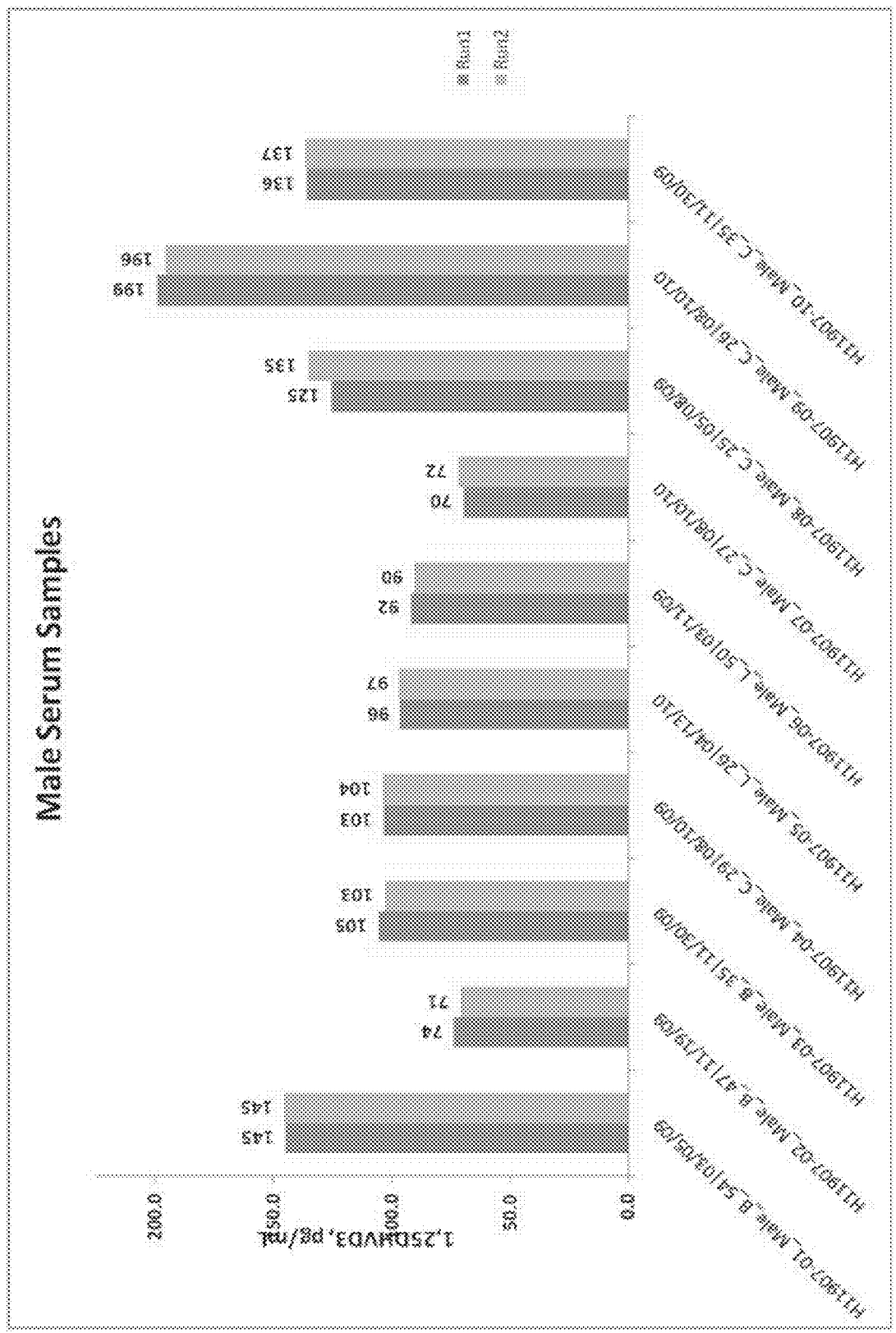
FIG. 24 shows the quantity of 1α,25-DihydroxyVitamin-$D_3$ detected in male serum samples from two runs, according to various embodiments of the present teachings.

FIG. 24 shows the quantity of 1α,25-DihydroxyVitamin-D$_3$ detected in male serum samples from two runs, according to various embodiments of the present teachings.

Figure 25:
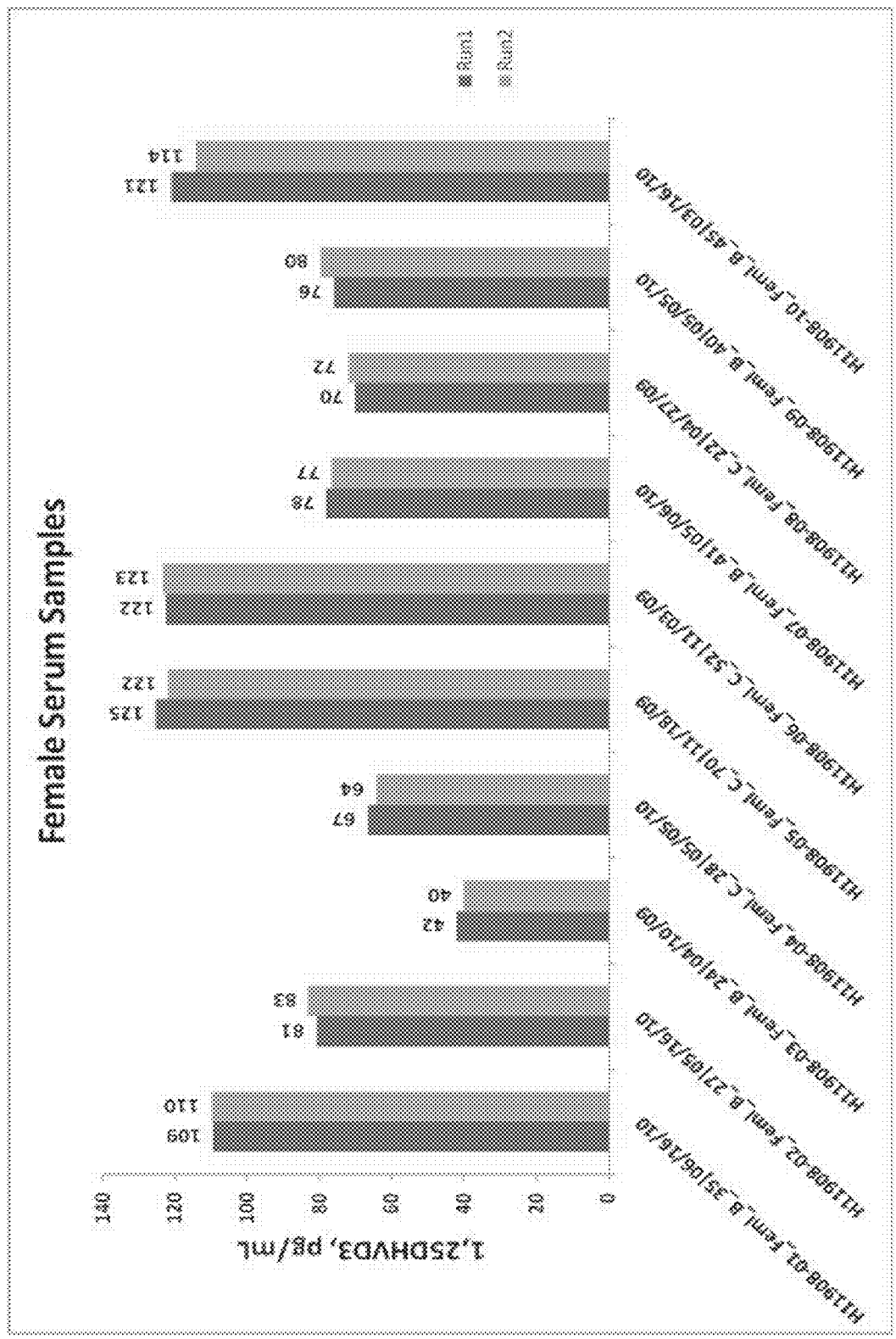
FIG. 25 shows the quantity of 1α,25-DihydroxyVitamin-$D_3$ detected in female serum samples from two runs, according to various embodiments of the present teachings.

FIG. 25 shows the quantity of 1α,25-DihydroxyVitamin-D$_3$ detected in female serum samples from two runs, according to various embodiments of the present teachings.

In some embodiments, the tagging chemistry and the method can be run on any triple quadrupole instruments, for example, those including FlashQuant™ with a Maldi source. Reagent kits, data analysis software, and the MS platform are provided in some embodiments as an analyzer for vitamin D3 and its metabolites. The same method can be employed for vitamin D2 and its metabolites.

Different liquid chromatography and mass spectrometry methods, systems, and software that can be used in accordance with various embodiments of the present teachings include those described in U.S. Provisional Patent Application No. 61/182,748 filed May 31, 2009, and in U.S. Patent Application No. US 2006/0183238 A1 which published on Aug. 17, 2006. Both of these references are incorporated herein in their entireties by reference.

According to various embodiments of the present teachings, a kit is provided that can comprise one or more of a dienophile reagent and an aminoxy MS tagging reagent. According to some embodiments, the aminoxy MS tagging reagent can comprise a compound having the following structure:

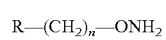

wherein R is

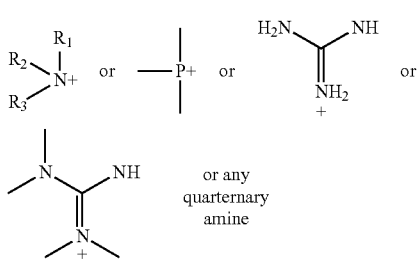

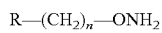

R₁, R₂, and R₃ can each independently be a hydrogen atom or an alkyl group, and n can be from 1 to 20, from 1 to 15, from 1 to 10, or from 1 to 5; or the structure:

R—(CH₂)$_n$—ONH₂ wherein R comprises one or more of these five structures

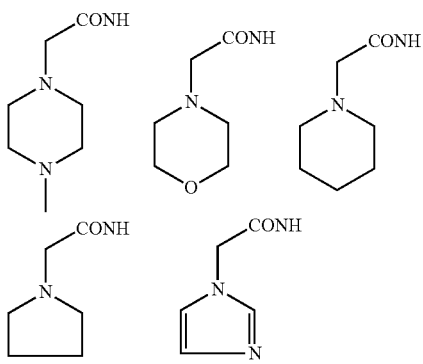

and n can be from 1 to 20, from 1 to 15, from 1 to 10, or from 1 to 5. In some embodiments, R can be any of the R groups described in connection with the tagging reagents of U.S. Pat. No. 7,195,751 to Pappin et al., which is incorporated herein in its entirety by reference.

In some embodiments, the kit can comprise at least one standard comprising a known concentration of a known vitamin D analyte. According to some embodiments, the aminoxy MS tagging reagent can be an isobaric tag from a set of isobaric tags and in some embodiments the kit can include a plurality of different isobaric tags from a set of isobaric tags. According to some embodiments, the aminoxy MS tagging reagent can be a mass differential tag from a set of mass differential tags and in some embodiments the kit can include a plurality of different mass differential tags from a set of mass differential tags. According to some embodiments, the kit can comprise a dienophile reagent, an aminoxy MS tagging reagent, a standard comprising a known vitamin D analyte and/or a known concentration of a known vitamin D analyte, and further can comprise instructions for labeling the vitamin D analyte.

Figure 12A:
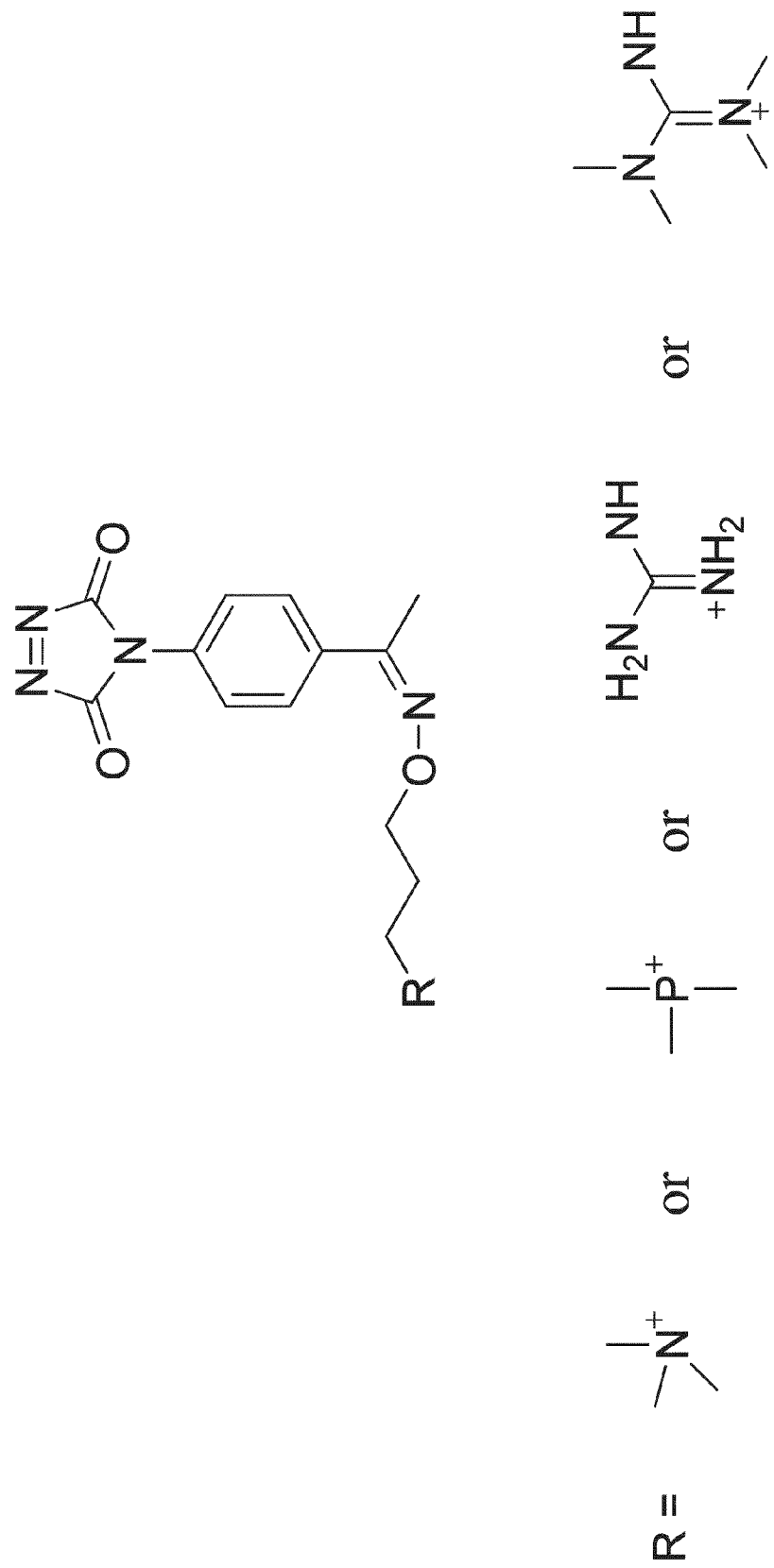
FIG. 12A shows a general formula and exemplary substituents that can be used in a one-step tagging method for vitamin D analytes.
Figure 13:
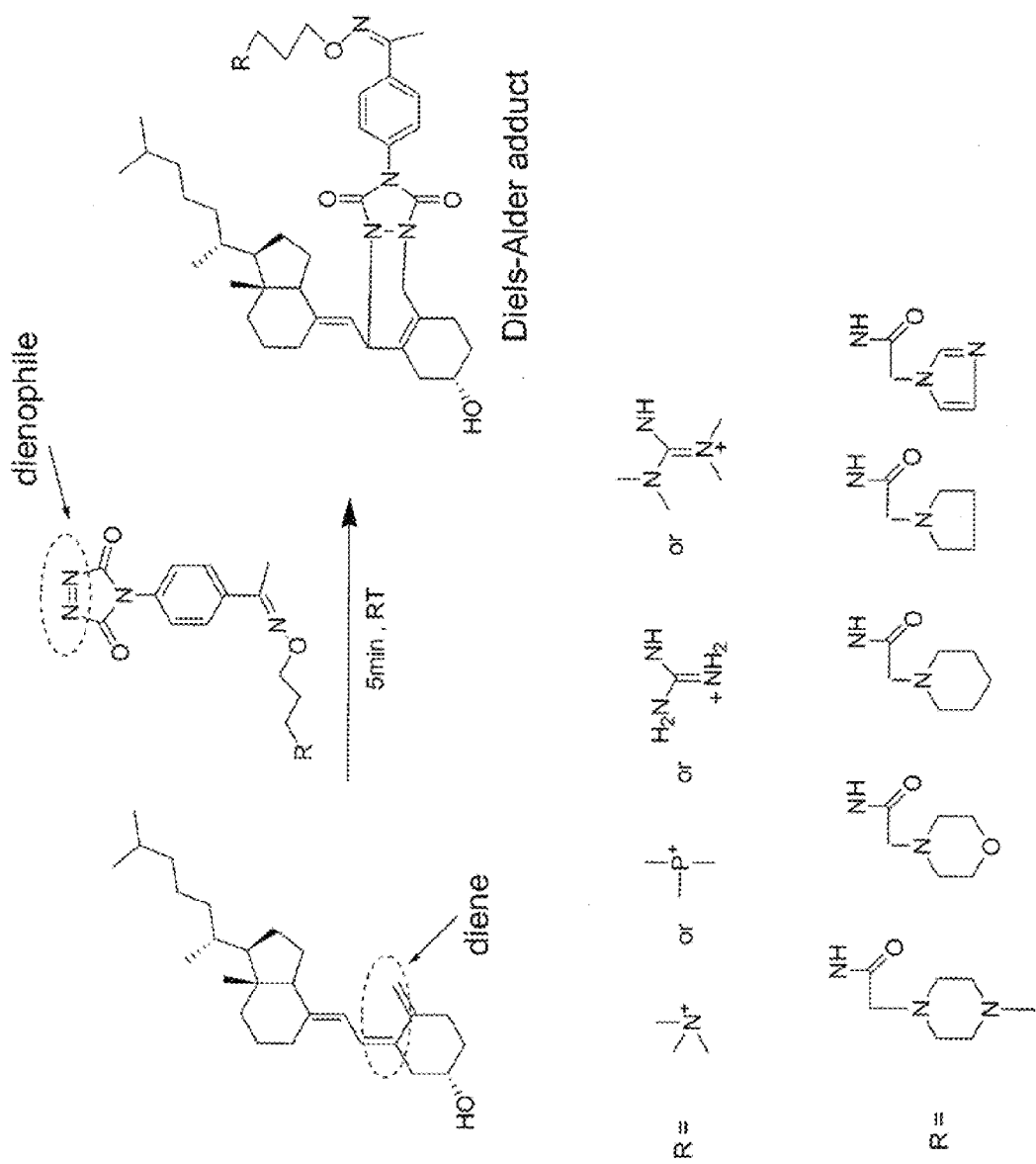
FIG. 13 shows a reaction scheme for a one-step chemical reaction, and exemplary substituents for the tagging molecule, that can be used to label vitamin D analytes according to various embodiments of the present teachings.

According to yet other embodiments of the present teachings, the kit can comprise a one-step tagging reagent as shown in FIG. 12A, a one-step tagging reagent as shown in FIG. 12B, a combination thereof, or the like. The kit can also comprise a standard comprising a known vitamin D analyte. In some embodiments, the standard can comprise a known concentration of a known vitamin D analyte. In some embodiments, the one-step tagging reagent included in the kit can comprise one or more isobaric tags from a set of isobaric tags. In some embodiments, the kit can comprise a plurality of different isobaric tags from a set of isobaric tags. In some embodiments, the one-step tagging reagent included in the kit can comprise one or more mass differential tags from a set of mass differential tags. In some embodiments, the kit can comprise a plurality of different mass differential tags from a set of mass differential tags.

According to various embodiments, the kit can comprise buffers, one or more chromatographic columns, and optionally other reagents and/or components useful in carrying out the assay. In some embodiments, the kit can comprise, for example, a homogeneous assay such that the user need only add a sample. In some embodiments, the kit can comprise calibration or normalization reagents or standards. Information pertaining to instrument settings that can or should be used to perform an assay can also be included in the kit. In some embodiments, information pertaining to sample preparation, operating conditions, volumetric amounts, temperature settings, and the like, is included with the kit.

The kit can be packaged in a hermetically sealed container containing one or more regent vessels and appropriate instructions. An electronic medium can be included in the kit, having stored thereon electronic information pertaining to one or more assays, measurement values, transition pairs, operating instructions, software for carrying out operations, a combination thereof, or the like.

According to various embodiments, a method can be provided for the synthesis of the QAOC reagent and its intermediates.

EXAMPLES

Aspects of the present teachings can be further understood in light of the following examples, which should not be construed as limiting the scope for the present teachings in any way.

Example 1

Illustration of the Steps in the Synthesis of the QAOC Reagent:

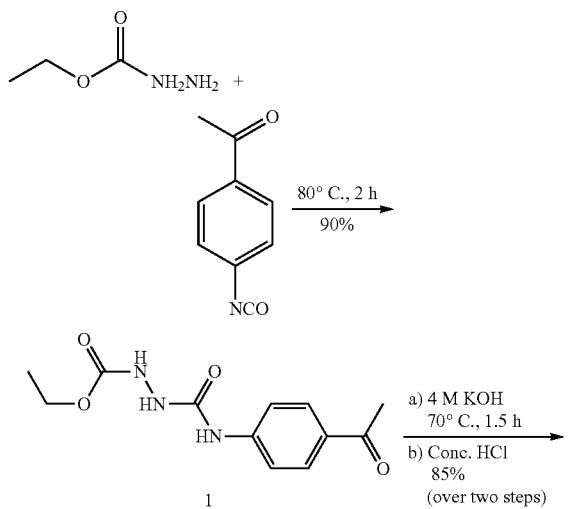

15

-continued

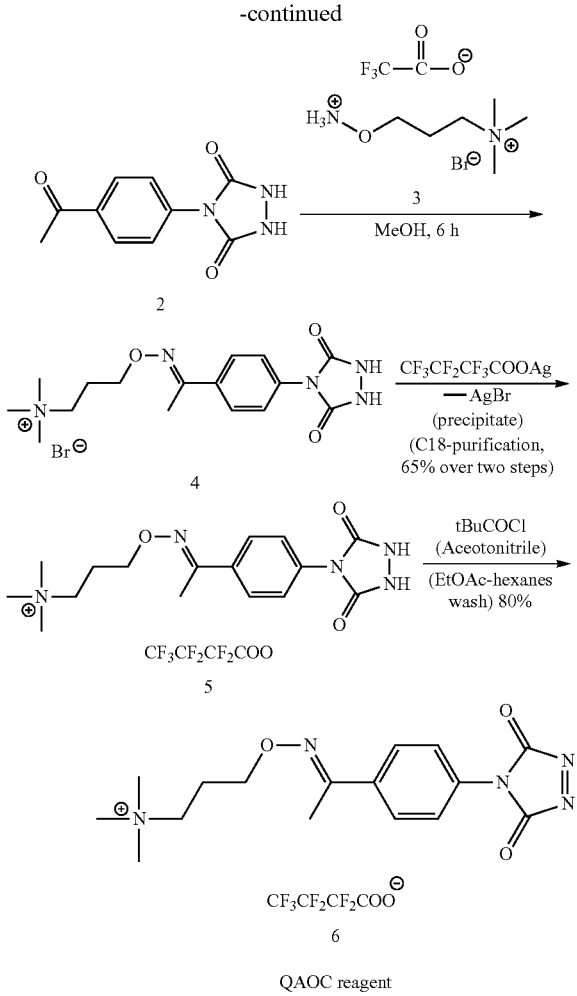

QAOC reagent

Synthesis of p-Acetyl-4-phenyl-1-carbethoxysemicarbazide (1)

To a solution of ethyl carbazate (6.46 g, 62.05 mmol) in toluene (100 mL) was added dropwise a solution of 4-acetylphenyl isocyanate (10 g, 62.05 mmol) in toluene (250 mL). The reaction mixture was stirred at room temperature for 2 h and then at 80° C. for 2 h. The precipitate formed in the reaction was filtered and dried in vacuum oven to give p-acetyl-4-phenyl-1-carbethoxysemicarbazide 1 (16.5 g, 90%). It was used without further purification in the next reaction step. (Synthesis adopted from: Organic Syntheses, Coll. Vol. 6, p. 936 (1988); Vol. 51, p. 121 (1971). 4-PHENYL-1,2,4-TRIAZOLINE-3,5-DIONE). In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

16

Synthesis of p-Acetyl-4-phenylurazole (2)

p-Acetyl-4-phenyl-1-carbethoxysemicarbazide 1 (15 g, 56 mmol) was heated with aqueous 4 M KOH solution (28 mL, 112 mmol) at 70° C. for about 2 h. Leftover granular solid was filtered off using a sintered filter funnel. Filtrate was cooled to room temperature and acidified with concentrated HCl. The precipitate formed was filtered and dried in vacuum oven to give p-acetyl-4-phenylurazole 2 as light yellow solid (12.4 g, 85%). $^1$H NMR (400 MHz, DMSO-d6): s=1.65 (s, 3H), 6.70 (d, 2H), 7.10 (d, 2H), 9.50 (s, 2H). (Synthesis adopted from: Organic Syntheses, Coll. Vol. 6, p. 936 (1988); Vol. 51, p. 121 (1971). 4-PHENYL-1,2,4-TRIAZOLINE-3,5-DIONE). In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Synthesis of p-Acetyl-4-phenylurazole quaternary aminooxy adduct bromide (4)

A suspension of p-Acetyl-4-phenylurazole 2 (2.10 g, 9.58 mmol) and quaternary aminooxy tag 3 (6.74 g, 20.6 mmol, in 100 mL of methanol-acetic acid (95:5 v/v) (the quaternary aminoxy tag as a labeling reagent is described in published U.S. application, 2011-0003395, incorporated herein in its entirety by reference), was stirred at ambient temperature for 48 h. HPLC analysis at this stage showed 95% conversion of 2 to the product p-Acetyl-4-phenylurazole quaternary aminooxy adduct 4. Column: DeltaPak C18, 3.9×150 mm, Buffer A: Water+0.1% TFA, Buffer B: Acetonitrile+0.085% TFA, Wavelength (Signal=254 nm, Reference=360nm), Flow=1 mL/min. Concentrations of analytes were approximately 0.25 mg/mL in methanol. Retention time of p-Acetyl-4-phenylurazole 2=5.1 min and p-Acetyl-4-phenylurazole quaternary aminooxy adduct 4=5.5 min. ES-MS data: M+ (calculated M+=$C_{16}H_{24}N_5O_3$+=334.19, observed M+=334.20 and 275.50 (-Me$_3$N)). Crude product was isolated as a white solid after removal of methanol. In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Counter ion exchange: The solid so obtained was dissolved in 40 mL of water and 30 mL (11.50 mmol of 4) of which was used for exchange. To this solution (in a 50 mL Falcon tube) a solution of silver heptafluoro butyrate (3.69 g, 11.53 mmol in 15 mL of deionized water) was added at once and mixed briefly by flipping the tube. Precipitate was separated by centrifugation at 3000 rpm for 2 min. Supernatant checked for any bromide ion (Br—) by addition of a dilute solution of silver heptafluoro butyrate (1 drop). Formation of turbidity indicates presence of Br—. To ensure complete precipitation of bromide ion another 0.2 equivalent (0.738 mg, in 5 mL water) of silver heptafluoro butyrate added, mixed, centrifuged and checked for Br—. A clear solution indicates total consumption of all Br—. Filtrate was taken in a syringe and filtered again through a 5 micron filter (25 mm, Millex LCR, PTEF, 25 mL/filter) and purified by flash chromatography (Purified in two batches: 43 g, C18 Isco column, Flow=40 ml/min, Solvent A: Water, Solvent B: Methanol, column equilibrated with 100 mL 50% B then 250 mL 2% B. Sample loaded as solution on column, 0-6 min 2% B then 6-35 min 2-85% B, wavelength =254 nm). Fractions containing product were analyzed by analytical HPLC for purity and pure (>95%) fractions were pooled and dried in a rotary evaporator to give p-Acetyl-4-phenylurazole quaternary aminooxy adduct heptafluoro butyrate 5 as white solid. Solid was co-evaporated with 20 mL of toluene and dried under vacuum to ensure complete removal of water. Final yield and HPLC purity was 2.6 g (65%) and >98%. In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Synthesis of OAO-C Reagent (6)

To a cold suspension of p-Acetyl-4-phenylurazole quaternary aminooxy adduct heptafluoro butyrate 5 (800 mg, 1.46 mmol, under argon atmosphere) a solution of tBuOCl (0.175 mL, 1.46 mmol in 7 mL of anhydrous acetonitrile) was added (2-3 min addition) dropwise while stirring. After addition is complete the reaction was stirred at 0-5° C. for 30 min. Acetonitrile was removed by a rotary evaporator (vented with nitrogen) and the pink solid was washed with anhydrous EtOAc (removed by pasture pipette from top under a blanket of argon). 0.65 g (80%) of 6 was obtained as an orange-red solid after drying under vacuum. Product was stored at −40° C., free of moisture and protected from bright light. In various aspects, the values of each of the components used in this example can be increased or decreased by an amount in the range of from about 5% to about 20%, for example, each component can be used in an amount that is from 5% less to 5% more than the value used in this example, each component can be used in an amount that is from 10% less to 10% more than the value used in this example, each component can be used in an amount that is from 15% less to 15% more than the value used in this example, or each component can be used in an amount that is from 20% less to 20% more than the value used in this example. In various aspects, the values can be varied by about plus or minus 5% to 20%.

Other Chemicals and Reagents Used for Sample Preparation and Analysis:
1. Internal Standard: 1α,25-DihydroxyVitamin-D$_3$ (26,26,26,27,27,27-d$_6$). [d6-1,25 DHVD$_3$]
   Source: Medical Isotopes Inc. Pelham, N.H. Product Number: D3222, 1 mg.

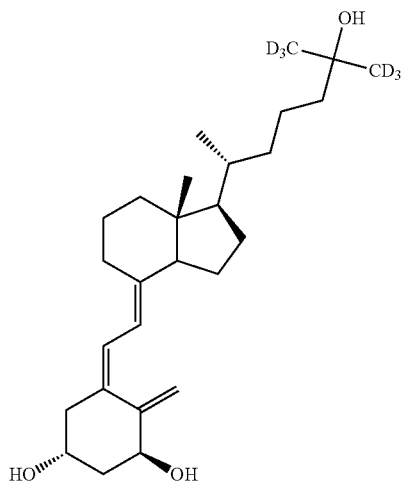

Chemical Formula: $C_{27}H_{38}D_6O_3$
Exact Mass: 422.37
Molecular Weight: 422.67

2. Analyte: 1α,25-DihydroxyVitamin-D$_3$
   Source: TRC, Canada. Product Number: C144500, 1 mg.

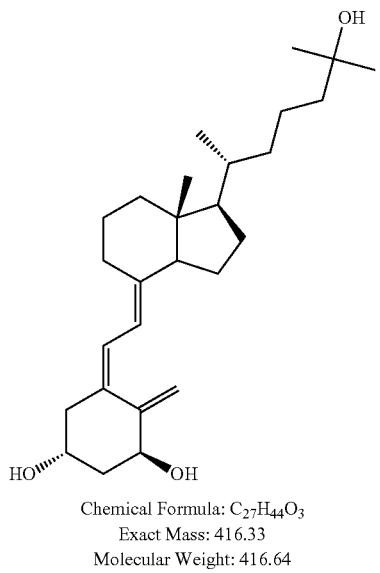

Chemical Formula: $C_{27}H_{44}O_3$
Exact Mass: 416.33
Molecular Weight: 416.64

3. Solvents:
   a) Di-isopropyl ether: Source: Aldrich, Product Number 38279
   b) Hexanes (HPLC Grade): Source: JT BAKER, Product Number 9304-03
   c) Iso-Propanol (i-PrOH): Source: Aldrich, Product Number 278475
   d) Methanol (HPLC Grade): Source, ACROS, AC61009-0040
   e) Acetonitrile (HPLC grade): Source, EMD, Product Number AX0145-1
   f) De-ionized water
   g) Formic acid (MS grade): Source, Fluka, Product Number 56302
   h) Dimethyl Formamide (DMF): Source, Aldrich, Product Number 270547

4. HPLC and Solid Phase Cartridges and Supplies:
   a) Chromabond 24 position collection rack: Source, Macherey Nagel, Product Number 730508.
   b) Chromabond Adaptor for comb. diff. Columns: Source, Macherey Nagel, Product Number 730101
   c) Chromabond columns XTR, 6 ml, 1000 mg BIG: Source, Macherey Nagel, Product Number 730487.250
   d) Sep-Pak® Vac Silica cartridge 6 cc/500 mg 55-105 μm 30/box: Source, Waters, Product Number WAT043400
   e) 5 mL PP vials: Source, VWR, Product Number 16465-262
   f) VWR® Culture Tubes, Disposable, Flint Glass 16×150 mm: Source, VWR, Product Number 60825-435
   g) Micro centrifuge Tubes 1.7 mL: Source, National Scientific, Product Number 20172-698
   h) Micro centrifuge Tubes 0.65 mL: Source, National Scientific, Product Number 20172-910
   i) HPLC Vials and caps: Source, Agilent, Product Numbers 9301-0978 and 5182-0540
5. Instrumentation and HPLC columns:
   a) Speed vacuum concentrator with rotors for 13 mm vials and 0.65 mL centrifuge tubes.
   b) Mini centrifuge
   c) Thermolyne Vortex Shaker
   d) Timer
   e) 5500 QTRAP Mass Spectrometer
   f) Shimadzu UPLC
   g) ACQUITY UPLC BEH C18 Column, 2.1×100 mm, 1.7 μm, Product number 186002352
   h) Necessary vial racks and holders
   i) 5 mL, 1 mL, 200 μL and 20 μL pipettes to be used (recommended) with RT 1000F, RT 200F and RT 20F tips from Rainin to avoid cross contamination.

Solid Phase Extraction and Derivatization Method
1. Spike internal standard (150 pg d6-1,25 DHVD$_3$ in 15 μL DMF) on silica cartridge.
2. Assemble Chromabond XTR and Silica cartridges using an adapter on collection rack. Chromabond XTR cartridge will be on top. Place glass tubes under the silica cartridge to collect washings.
3. Equilibrate plasma or serum sample to ambient temperature, vortex briefly to obtain an even suspension and dispense 200 μL in a 1.7 mL micro centrifuge tube. Dilute with 700 μL of water, vortex for 30 sec and spin down.
4. Load diluted sample on Chromabond XTR column and wait 10 min. (use timer)
5. Elute Chromabond XTR column with Di-isopropyl ether (4×1 mL) on to Silica column. Wait 3 min in between elution steps (use timer).
6. Remove and dispose Chromabond XTR column and wash Silica column with 4% (2×4.5 mL) and 6% (2×3 mL) iPrOH in hexanes. Discard the washings and glass tubes.
7. Elute 1,25 DHVD$_3$ with 25% iPrOH in hexanes (4.5 mL) in a 5 mL tube and dry in a speed vac. at ambient temperature.
8. Add 300 μL of MeOH to the 5 mL tube, vortex for 1 min, spin down, transfer the MeOH solution to a 0.65 mL micro-centrifuge tube and dry in a speed vac. at ambient temperature.
9. Derivatization: Add QAO-Cookson reagent (20 μL, 0.5 mg/mL in acetonitrile) to the 0.65 mL micro-centrifuge tube vortex for 15 sec, spin down. Repeat the vortexing step once more after you are done with the first round of vortexing of all the samples. Spin down all tubes and wait for 30 min at ambient temperature.

The QAO-Cookson reagent solution can be freshly made from solid reagent and used within 1 hour of the derivatization step. Reagent has good solubility up to a concentration of 2 mg/mL in acetonitrile.

10. Add 20 μL water, mix, spin down and transfer the solution to a HPLC vial and analyze.

LC-MS Method
Comment: DHVD3_C18_2.1×100 mm 1.7uAcquity_08530254156 21_Dec02_2010
Synchronization Mode: LC Sync
Auto-Equilibration: Off
Acquisition Duration: 3 min60 sec
Number Of Scans: 774
Periods In File: 1
Acquisition Module: Acquisition Method
Software version Analyst 1.5.1
MS Method Properties:
Period 1:
Scans in Period: 774
Relative Start Time: 0.00 msec
Experiments in Period: 1
Period 1 Experiment 1:
Scan Type: MRM (MRM)
Scheduled MRM: No
Polarity: Positive
Scan Mode: N/A
Ion Source: Turbo Spray
Resolution Q1: Unit
Resolution Q3: Unit
Intensity Thres.: 0.00 cps
Settling Time: 0.0000 msec
MR Pause: 5.0070 msec
MCA: No
Step Size: 0.00 Da
@Q1 Mass (Da) Q3 Mass (Da) Dwell(msec) Param Start Stop ID 748.500 689.400 150.00 d0DHVD3(1,25:24,25,23:25)_NeuL
@Q1 Mass (Da) Q3 Mass (Da) Dwell(msec) Param Start Stop ID 754.540 695.400 150.00 d6DHVD3(1,25:24,25:23,25)_NeuL
Parameter Table(Period 1 Experiment 1):
CUR: 25.00
IS: 3500.00
TEM: 650.00
GS1: 50.00
GS2: 55.00
CAD: Medium
DP 80.00
EP 10.00
CE 43.00
CXP 15.00
Integrated Harvard Syringe Pump Method Properties (Not Used)
Syringe Diameter (mm): 4.61
Flow Rate: 7.000 uL/min
Valco Valve Diverter
Total Time (min) Position
1 0.0 B
2 1.0 A
3 4.0 B
Shimadzu LC Method Properties
Shimadzu LC system Equlibration time=4.00 min
Shimadzu LC system Injection Volume=20.00 ul
Shimadzu LC Method Parameters
Pumps
Pump A Model: LC-20AD
Pump B Model: LC-20AD Pumping Mode: Binary Flow
Total Flow: 0.7000 mL/min.
Pump B Conc: 5.0%
B Curve: 0
Pressure Range (Pump A/B): 0-1422 psi
Autosampler
Model: SIL-20AC
Rinsing Volume: 200 uL
Needle Stroke: 52 mm.
Rinsing Speed: 35 uL/sec.
Sampling Speed: 15.0 uL/sec.
Purge Time: 25.0 min.
Rinse Dip Time: 0 sec.
Rinse Mode: Before and after aspiration
Cooler Enabled: Yes
Cooler Temperature: 5 deg. C
Control Vial Needle Stroke: 52 mm
Pump Method: Rinse Port Only
Rinse Time: 2 sec
Oven
Model: CTO-20A
Temperature Control: Enabled
Temperature: 40 deg. C
Max. Temperature: 50 deg. C
System Controller
Model: CBM-20A
Power: On
Event 1: Off
Event 2: Off
Event 3: Off
Event 4: Off
Time Program
Time Module Events Parameter
0.20 Pumps Pump B Conc. 5
0.30 Pumps Pump B Conc. 35
5.00 Pumps Pump B Conc. 50
5.50 Pumps Pump B Conc. 95
6.00 Pumps Pump B Conc. 95
6.05 System Controller Stop Other embodiments of the present teachings will be apparent to those skilled in the art from consideration of the present specification and practice of the present teachings disclosed herein. It is intended that the present specification and examples be considered exemplary only.

What is claimed:

1. A method for quantitating a vitamin D analyte in a sample, the vitamin D analyte comprising one or more of vitamin D2, vitamin D3, a metabolite of vitamin D2, and a metabolite of vitamin D3, the method comprising:
    treating a vitamin D analyte with a dienophile-containing one-step tagging reagent to form a labeled Diels-Alder adduct;
    providing a standard comprising a known concentration of a known vitamin D analyte;
    treating the known vitamin D analyte in the standard with a one-step dienophile-containing labeled Diels-Alder reagent to form a labeled standard adduct;
    mixing the labeled standard adduct and the labeled Diels-Alder adduct to form a mixture;
    separating the mixture to form separated labeled analytes; and
    analyzing the labeled Diels-Alder adduct using mass spectrometry;
    wherein analyzing the labeled Diels-Alder adduct comprises analyzing the separated labeled analytes and wherein the one-step dienophile-containing labeled Diels-Alder reagent used to label the standard comprises a first isobaric tag from a set of isobaric tags and the dienophile-containing one-step tagging reagent used to form the labeled Diels-Alder adduct comprises a second isobaric tag from the set of isobaric tags, that differs from the first isobaric tag.

2. The method of claim 1, wherein the one-step tagging reagent comprises compounds having the following structure:

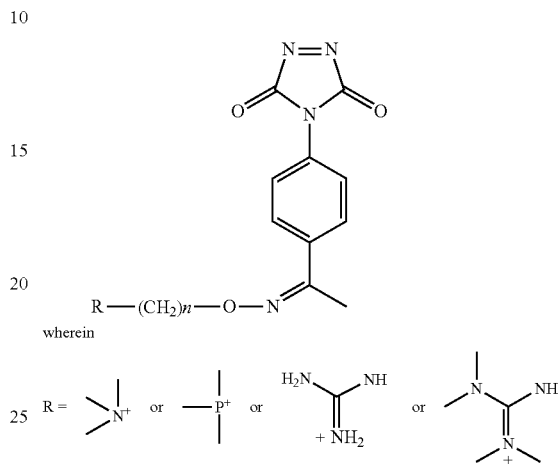

wherein and n is from 1 to 20.

3. The method of claim 1, wherein the one-step tagging reagent comprises compounds having the following structure:

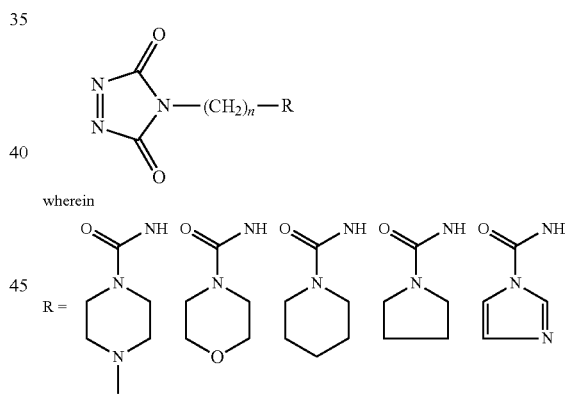

wherein and n is from 1 to 20.

4. The method of claim 1, wherein analyzing the labeled adduct using mass spectrometry comprises using LC-MSMS analysis of the labeled adduct.

5. The method of claim 4, further comprising parent daughter ion transition monitoring (PDITM) of the labeled analytes using a triple quadrupole MS platform.

6. The method of claim 1, wherein the vitamin D analyte comprises a plurality of different vitamin D analytes, and the labeling comprises labeling with a plurality of different tagging reagents.

7. The method of claim 6, wherein the plurality of different tagging reagents comprises isobaric tags.

8. The method of claim 7, wherein the isobaric tags are selected from the following structures:

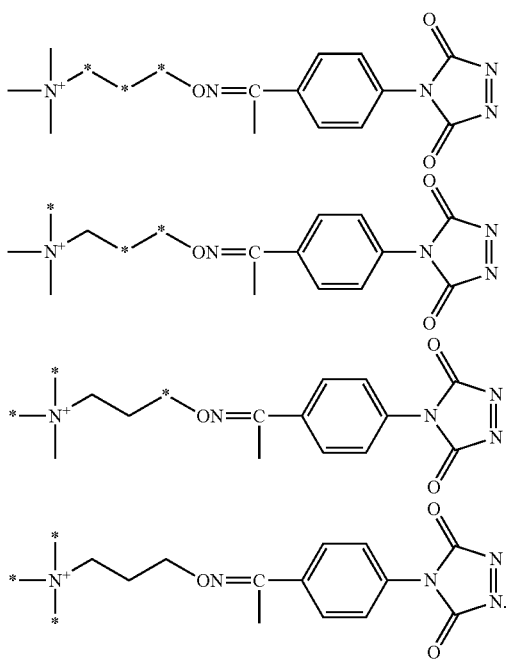

9. The method of claim 6, wherein the plurality of different tagging reagents comprises mass differential tags.

10. The method of claim 9, wherein the mass differential tags are selected from the following structures:

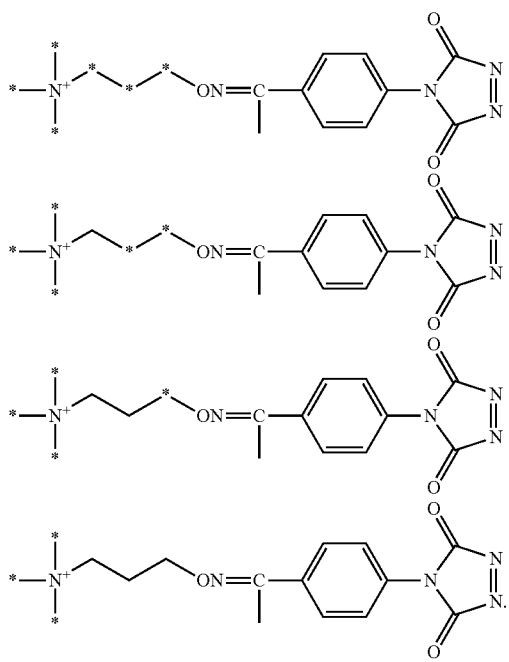

11. The method of claim 1, wherein the metabolites of vitamin D2 comprise a monohydroxy metabolite and/or a dihydroxy metabolite of vitamin D2.

12. The method of claim 1, wherein the metabolites of vitamin D3 comprise a monohydroxy metabolite and/or a dihydroxy metabolite of vitamin D3.

13. A method for quantitating a vitamin D analyte in a sample, the vitamin D analyte comprising one or more of vitamin D2, vitamin D3, a metabolite of vitamin D2, and a metabolite of vitamin D3, the method comprising:
treating a vitamin D analyte with a dienophile reagent to form a Diels-Alder adduct;
labeling the Diels-Alder adduct with an aminoxy mass spectrometry (MS) tagging reagent to form a labeled adduct; and
analyzing the labeled adduct using mass spectrometry.

14. The method of claim 13, wherein the aminoxy MS tagging reagent comprises compounds having the following structure:

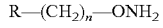

wherein R is

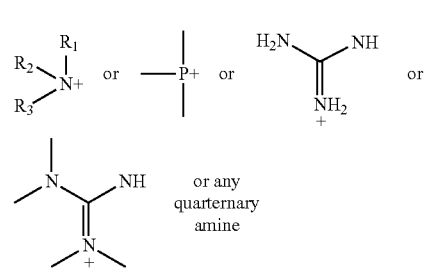

$R_1$, $R_2$, and $R_3$ is each independently a hydrogen atom or an alkyl group, and n is from 1 to 20.

15. The method of claim 13, wherein the aminoxy MS tagging reagent comprises compounds having the following structure:

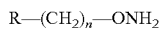

wherein R comprises one or more of these five structures

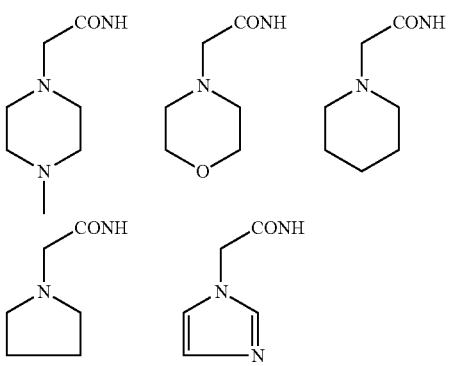

and n is from 1 to 20.

16. The method of claim 13, further comprising:
providing a standard comprising a known concentration of a known vitamin D analyte;
treating the known vitamin D analyte in the standard with a dienophile reagent to form a standard Diels-Alder adduct;
labeling the standard Diels-Alder adduct with an aminoxy MS tagging reagent to form a labeled standard adduct;
mixing the labeled standard adduct and the labeled adduct to form a mixture; and
separating the mixture to form separated labeled analytes;
wherein analyzing the labeled adduct comprises analyzing the separated analytes.

17. The method of claim 16, wherein the aminoxy MS tagging reagent used to label the standard Diels-Alder adduct comprises a first isobaric tag from a set of isobaric tags and the aminoxy MS tagging reagent used to label the Diels-Alder adduct comprises a second isobaric tag from the set of isobaric tags, that differs from the first isobaric tag.

18. The method of claim 13, wherein analyzing the labeled adduct using mass spectrometry comprises using LC-MSMS analysis of the labeled adduct.

19. The method of claim 18, further comprising parent daughter ion transition monitoring (PDITM) of the labeled analytes using a triple quadrupole MS platform.

20. The method of claim 18, wherein the labeled adduct undergoes neutral loss during MSMS and leaves a reporter ion that is a charged analyte species.

21. The method of claim 18, wherein the labeled adduct loses a charged fragment during MSMS.

22. The method of claim 18, wherein the aminoxy MS tagging reagent forms a reporter ion that is a tag fragment during MSMS.

23. The method of claim 13, wherein the vitamin D analyte comprises a plurality of different vitamin D analytes, and the labeling comprises labeling with a plurality of different tagging reagents.

24. The method of claim 23, wherein the plurality of different tagging reagents comprises isobaric tags.

25. The method of claim 24, wherein the isobaric tags are selected from the following structures:

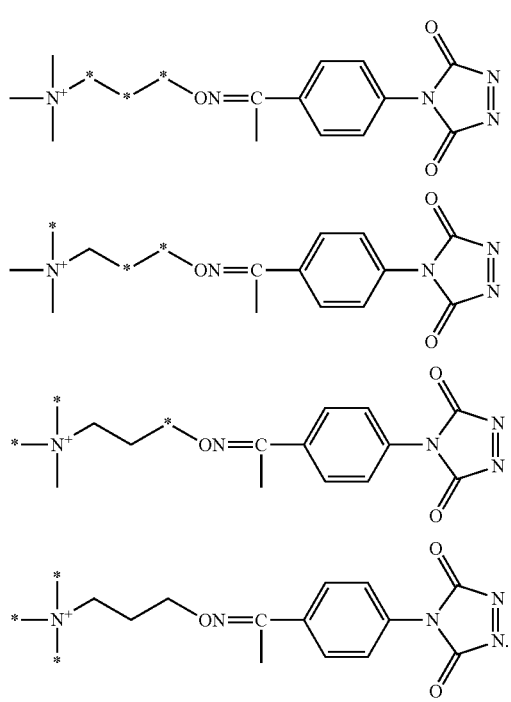

26. The method of claim 23, wherein the plurality of different tagging reagents comprises mass differential tags.

27. The method of claim 26, wherein the mass differential tags are selected from the following structures:

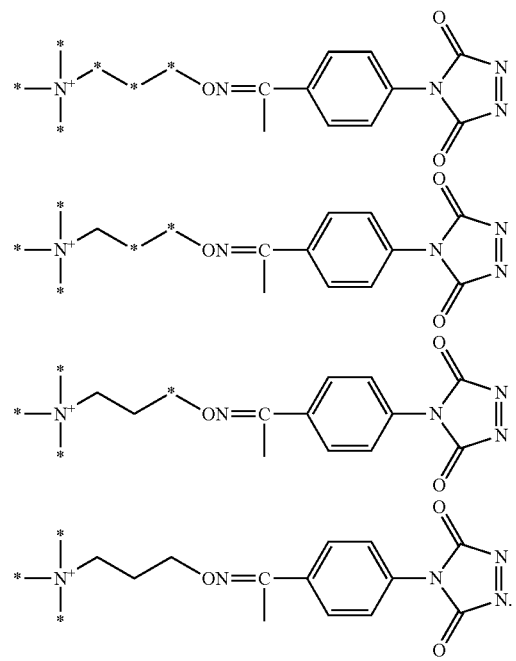

28. The method of claim 13, wherein the metabolites of vitamin D2 comprise a monohydroxy metabolite and/or a dihydroxy metabolite of vitamin D2.

29. The method of claim 13, wherein the metabolites of vitamin D3 comprise a monohydroxy metabolite and/or a dihydroxy metabolite of vitamin D3.

30. A kit comprising a dienophile reagent and an aminoxy MS tagging reagent, in a package.

31. The kit of claim 30, wherein the aminoxy MS tagging reagent comprises a mass differential tag from a set of mass differential tags, and the kit further includes a plurality of different aminoxy MS tagging reagents respectively comprising mass differential tags from the set of mass differential tags.

32. The kit of claim 30, wherein the aminoxy MS tagging reagent comprises a compound having the following structure $$R\text{—}(CH_2)_n\text{—}ONH_2$$

wherein R is

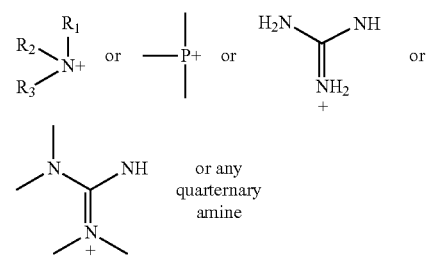

$R_1$, $R_2$, and $R_3$ is each independently a hydrogen atom or an alkyl group, and n is from 1 to 20.

33. The kit of claim 30, wherein the aminoxy MS tagging reagent comprises a compound having the following structure $$R\text{—}(CH_2)_n\text{—}ONH_2$$

wherein R comprises one or more of these five structures

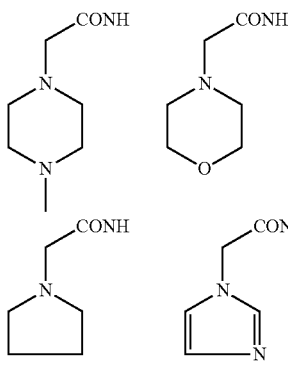

and n is from 1 to 20.

34. The kit of claim 30, further comprising a standard comprising a known vitamin D analyte.

35. The kit of claim 30, further comprising a standard comprising a known concentration of a known vitamin D analyte.

36. The kit of claim 30, wherein the aminoxy MS tagging reagent comprises an isobaric tag from a set of isobaric tags, and the kit further includes a plurality of different aminoxy MS tagging reagents respectively comprising isobaric tags from the set of isobaric tags.

37. The kit of claim 30, further comprising instructions for labeling a vitamin D analyte.

38. A kit comprising a dienophile-containing labeled Diels Alder reagent, in a package
wherein the labeled Diels Alder reagent comprises a compound having the formula:

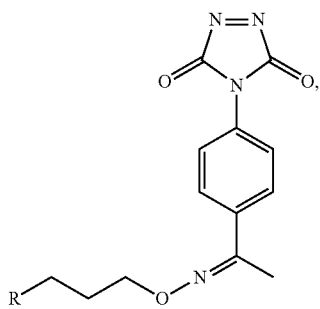

wherein R is

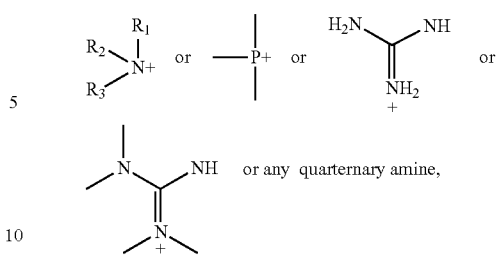

and $R_1$, $R_2$, and $R_3$ is each independently a hydrogen atom or an alkyl group;
or the labeled Diels Alder reagent comprises a compound having the formula:

$$\text{triazoledione}-N-(CH_2)_n-R,$$

wherein

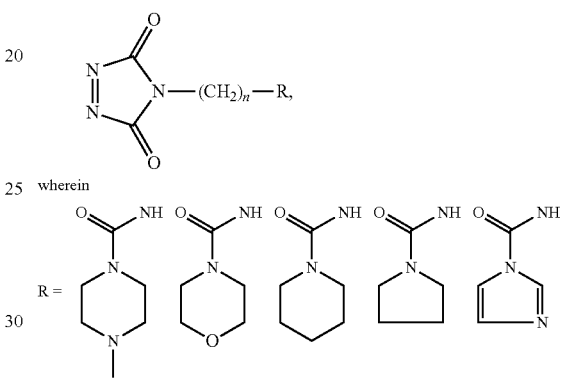

and n is from 1 to 20.

39. The kit of claim 38, further comprising a standard comprising a known vitamin D analyte.

40. The kit of claim 38, further comprising a standard comprising a known concentration of a known vitamin D analyte.

41. The kit of claim 38, wherein the labeled Diels Alder reagent comprises an isobaric tag from a set of isobaric tags, and the kit further includes a plurality of different one-step tagging reagents comprising respective isobaric tags from the set of isobaric tags.

42. The kit of claim 38, further comprising instructions for labeling a vitamin D analyte.

43. The kit of claim 38, wherein the labeled Diels Alder reagent comprises a mass differential tag from a set of mass differential tags, and the kit further includes a plurality of different one-step tagging reagents comprising respective mass differential tags from the set of mass differential tags.

* * * * *